(12) United States Patent
Wagers et al.

(10) Patent No.: US 8,323,967 B2
(45) Date of Patent: Dec. 4, 2012

(54) ENHANCING STEM CELL MOBILIZATION

(75) Inventors: Amy Wagers, Brookline, MA (US); Irene Min, Ithaca, NY (US)

(73) Assignee: Joslin Diabetes Center, Inc., Boston, MA (US)

( * ) Notice: Subject to any disclaimer, the term of this patent is extended or adjusted under 35 U.S.C. 154(b) by 525 days.

(21) Appl. No.: 12/295,680

(22) PCT Filed: Apr. 5, 2007

(86) PCT No.: PCT/US2007/066079
§ 371 (c)(1), (2), (4) Date: May 11, 2009

(87) PCT Pub. No.: WO2007/118157
PCT Pub. Date: Oct. 18, 2007

(65) Prior Publication Data
US 2009/0220453 A1   Sep. 3, 2009

Related U.S. Application Data

(60) Provisional application No. 60/789,468, filed on Apr. 5, 2006.

(51) Int. Cl.
| | |
|---|---|
| *C12N 5/071* | (2010.01) |
| *C12N 5/00* | (2006.01) |
| *C12N 5/02* | (2006.01) |
| *C12N 15/11* | (2006.01) |
| *A01N 1/02* | (2006.01) |
| *C07H 21/04* | (2006.01) |

(52) U.S. Cl. ............ 435/372; 435/375; 435/377; 435/2; 514/44 A; 536/24.5

(58) Field of Classification Search .................. None
See application file for complete search history.

(56) References Cited

U.S. PATENT DOCUMENTS

| | | | |
|---|---|---|---|
| 5,206,152 A | 4/1993 | Sukhatme | |
| 6,008,048 A | 12/1999 | Monia et al. | |
| 6,200,960 B1 * | 3/2001 | Khachigian | 514/44 A |
| 6,869,704 B1 | 3/2005 | Qi et al. | |
| 6,969,704 B1 | 11/2005 | Pinsky et al. | |
| 2003/0157030 A1 * | 8/2003 | Davis et al. | 424/46 |

OTHER PUBLICATIONS

Kukita et al. Endocrinology 1997, 138(10) 4384-4389.*
McCoy et al.; 12-O-Tetradecanoylphorbol-13-Acetate Activation of the MDR 1 Promoter is Mediated by EGR1.; Molecular and Cellular Biology; vol. 15; No. 11; Nov. 1995; pp. 6100-6108.
Min et al.; The Transcription Factor EGR1 Controls Both the Proliferation and Localization of Hematopoietic Stem Cells; Cell Stem Cell; vol. 2; Apr. 2008; pp. 380-391; (includes 18 pages of Supplemental Data).
International Search Report and Written Opinion from International Application No. PCT/US07/66079, filed Apr. 5, 2007; mailed Sep. 24, 2007.
Min et al.; Molecular Mediators of Hematopoietic Stem Cell Expansion and Migration; Abstract from ISSCR Meeting; Jun. 2004.
Nguyen et al.; The Zinc Finger Transcription Factor EGR-1 is Essential for and Restricts Differentiation Along the Macrophage Linage; Cell; vol. 72; Issue 2; Jan. 29, 1993; pp. 197-209 (Abstract only).
Neyses et al.; Inhibition of Endotheline-1 Induced Myocardial Protein Synthesis by an Antisense Oligonucleotide Against the Early Growth Response Gene-1; Biochemical and Biophysical Research Communications; vol. 181; Issue 1; Nov. 27, 1991; pp. 22-27 (Abstract only).
Garnett et al.; Differential Gene Expression Between Zucker Fatty Rats and Zucker Diabetic Fatty Rats: A Potential Role for the Immediate-Early Gene Egr-1 in Regulation of Beta Cell Proliferation; Journal of Molecular Endocrinology; vol. 35; Issue 1; Aug. 2005; pp. 13-25 (Abstract only).
Banks et al.; Egr-1 Antisense Oligonucleotides Inhibit Hypoxia-Induced Proliferation of Pulmonary Artery Adventitial Fibroblasts; Journal of Applied Physiology; vol. 98; No. 2; Feb. 2005; pp. 732-738 (Abstract only).
Baron et al.; Antisense to the Early Growth Response-1 Gene (Egr-1) Inhibits Prostate Tumor Development in TRAMP Mice; New York Academy of Sciences; vol. 1002; Dec. 2003; pp. 197-216 (Abstract only).
Baron et al.; Inhibition of Egr-1 Expression Reverses Transformation of Prostate Cancer Cells In Vitro and In ViVo; Oncogene; vol. 22; Issue 27; Jul. 3, 2003; pp. 4194-4204 (Abstract only).
Fahmy et al.; Antisense Egr-1 RNA Driven by the CMV Promoter is an Inhibitor of Vascular Smooth Muscle Cell Proliferation and Regrowth after Injury; Journal of Cellular Biochemistry; vol. 87; Issue 3; 2002; pp. 575-582 (Abstract only).
Ostrowski et al.; Experimental Therapeutics; British Journal of Cancer; vol. 88; 2003; pp. 1143-1151 (Abstract only).
Khachigian; DNAzymes: Cutting Path to a New Class of Therapeutics; Current Opinion in Molecular Therapeutics; vol. 4; Issue 2; 2002; pp. 119-121.
Forsberg et al.; Differential Expression of Novel Potential Regulators in Hematopoietic Stem Cells; PLoS Genetics; vol. 1; Issue 3; Sep. 2005; pp. 0281-0294.
Muthukkumar et al.; Role of Egr-1 Gene Expression in B Cell Receptor-Induced Apoptosis in an Immature B Cell Lymphoma; The Journal of Biological Chemistry; vol. 272; No. 44; Oct. 31, 1997; pp. 27897-27993.
Okada et al.; Extinguishing Egr-1-Dependent Inflammatory and Thrombotic Cascades after Lung Transplantation; The FASEB Journal; vol. 15; No. 14; pp. 2757-2759, 2001.

(Continued)

*Primary Examiner* — Doug Schultz
(74) *Attorney, Agent, or Firm* — Pierce Atwood LLP; Joseph M. Maraia; Kevin M. Farrell

(57) ABSTRACT

This invention relates to methods and compositions for enhancing hematopoietic stem cell mobilization by inhibiting early growth response-1 (egr1) activity.

17 Claims, 16 Drawing Sheets

OTHER PUBLICATIONS

Fahmy et al.; Locked Nucleic Acid Modified DNA Enzymes Targeting Early Growth Response-1 Inhibit Human Vascular Smooth Muscle Cell Growth; Nucleic Acids Research; vol. 32; No. 7; 2004; pp. 2281-2285.

Malkani et al.; An egr-1 [zif268] Antisense Oligodeoxynucleotide Infused into the Amygdala Disrupts Fear Conditioning; Learning & Memory; vol. 11; Issue 5; Sep. 2004; pp. 617-624.

Liu et al.; Transcription Factor EGR-1 Suppresses the Growth and Transformation of Human HT-1080 Fibrosarcoma Cells by Induction of Transforming Growth Factor β1; Proceedings of the National Academy of Sciences; vol. 93; Oct. 1996; pp. 11831-11836.

Cogswell et al.; Involvement of Egr-1/RelA Synergy in Distinguishing T Cell Activation from Tumor Necrosis Factor-α-induced NF-κB1 Transcription; Journal of Experimental Medicine; vol. 185, No. 3; Feb. 3, 1997; pp. 491-497.

Hofers et al.; Transcription Factor Egr-1 Regulates Glomerular Mesangial Cell Proliferation; The Journal of Biological Chemistry; vol. 271, No. 45; Nov. 8, 1996; pp. 28306-28310.

Kukita et al.; Regulation of Osteoclastogenesis by Antisense Oligodeoxynucleotides Specific to Zinc Finger Nuclear Transcription Factors Egr-1 and WT1 in Rat Bone Marrow Culture System; endo.endojournals.org.; vol. 13, No. 10; Oct. 1, 1997; pp. 4384-4389.

Morrison, et al.; Cyclophosphamide/Granulocyte Colony-Stimulating Factor Induces Hematopoietic Stem Cells to Proliferate Prior to Mobilization; Proceedings of the National Academy of Sciences; vol. 94; Mar. 1997; pp. 1908-1913.

Passagué, et al.; Global Analysis of Proliferation and Cell Cycle Gene Expression in the Regulation of Hematopoietic Stem and Progenitor Cell Fates; The Journal of Experimental Medicine; vol. 202, No. 11; Dec. 5, 2005; pp. 1599-1611.

Huang, et al.; Egr-1 Negatively Regulates Human Tumor Cell Growth via the DNA-binding Domain, Cancer Research; vol. 55; No. 21; Nov. 1, 1995; pp. 5054-5062.

Christy, et al.; DNA Binding Site of the Growth Factor-Inducible Protein Zif268; Proceedings of the National Academy of Sciences; vol. 86; Nov. 1989; pp. 8737-8741.

Jain, et al.; Casein Kinase II Associates with Egr-1 and Acts as a Negative Modulator of its DNA Binding and Transcription Activities in N1H 3T3 Cells; The Journal of Biological Chemistry; vol. 271, No. 23; Jun. 7, 1996; pp. 13530-13536.

Joslin, et al.; Haploinsufficiency of EGR1, A Candidate Gene in the del(5q), Leads to the Development of Myeloid Disorders; American Society of Hematology (bloodjournal.hematologylibrary.org); vol. 110, No. 2; Jul. 15, 2007; pp. 719-726.

Le Beau, et al.; Cytogenetic and Molecular Delineation of the Smallest Commonly Deleted Region of Chromosome 5 in Malignant Myeloid Diseases; Proceedings of the National Academy of Sciences USA; vol. 90; Jun. 1993; pp. 5484-5488.

Cheng, et al.; Hematopoietic Stem cell Quiescence Maintained by p21cip1/waf1; Science; vol. 287, No. 5459; Mar. 10, 2000; pp. 1804-1808 (Abstract only).

Laslo, et al.; Multilineage Transcriptional Priming and Determination of Alternate Hematopoietic Cell Fates; Cell; vol. 126, No. 4; Aug. 25, 2006; pp. 755-766 (Abstract only).

Lee, et al.; Unimpaired Thymic and Pheripheal T Cell Death in Mice Lacking the Nuclear Receptor NGFI-B (Nur77); Science; vol. 269, No. 5223; Jul. 28, 1995; pp. 532-535 (Abstract only).

Schnell, et al.; Early Growth Response Gene 1 Provides Negative Feedback to Inhibit Entry of Progenitor Cells into the Thymus; The Journal of Immunology; vol. 176; Jan. 26, 2006; pp. 4740-4747.

Schnell, et al.; Control of Recent Thymic Emigrant Survival by Positive Selection Signals and Early Growth Response Gene 1; The Journal of Immunology; vol. 175; Jun. 10, 2005; pp. 2270-2277.

Dinkel, et al.; The Transcription Factor Early Growth Response 1 (Egr-1) Advances Differentiation of Pre-B and Immature B Cells; Journal of Experimental Medicine; vol. 188, No. 12; Dec. 21, 1998; pp. 2215-2224.

Krishnaraju, et al.; Early Growth Response Gene 1 Stimulates Development of Hematopoietic Progenitor Cells along the Macrophage Lineage at the Expense of the Granulocyte and Erythroid Lineages; Blood; vol. 97, No. 5; Mar. 1, 2001; pp. 1298-1305.

Bettini, et al.; Thymocyte Development in Early Growth Response Gene 1-Deficient Mice; The Journal of Immunology; vol. 169; Jun. 6, 2002; pp. 1713-1720.

Lee, et al.; Unimpaired Macrophage Differentiation and Activation in Mice Lacking the Zinc Finger Transcription Factor NGFI-A (EGR1); Molecular and Cellular Biology; vol. 16, No. 8; Aug. 1996; pp. 4566-4572.

Lee, et al., Growth and Differentiation Proceeds Normally in Cells Deficient in the Immediate Early Gene NGFI-1; The Journal of Biological Chemistry; vol. 270, No. 17; Apr. 28, 1995; pp. 9971-9977.

* cited by examiner

Figure 1A
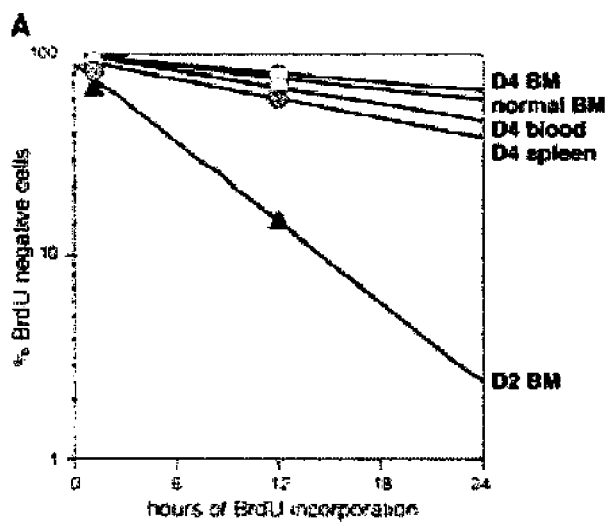
| Figure 1B | Figure 1C | Figure 1D | Figure 1E | Figure 1F |
|---|---|---|---|---|
| normal BM HSC | D2 BM HSC | D4 BM HSC | D4 spleen HSC | D4 blood HSC |
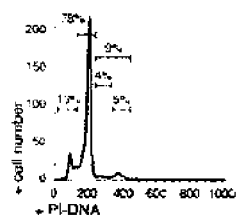 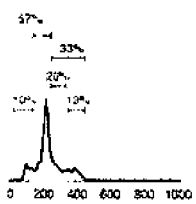 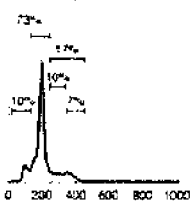 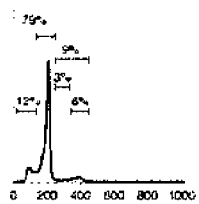
Figure 2A                                   Figure 2B
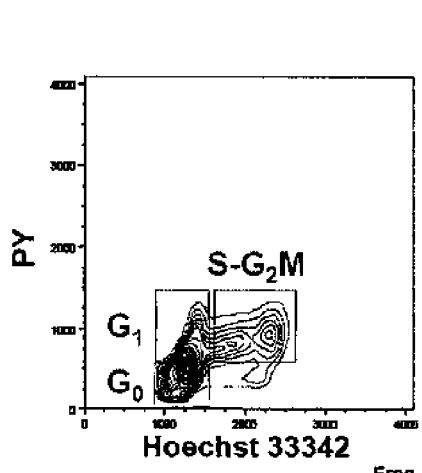 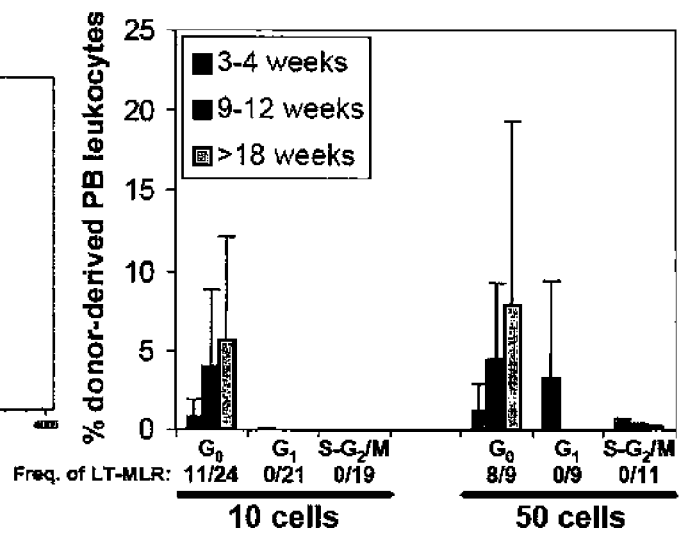

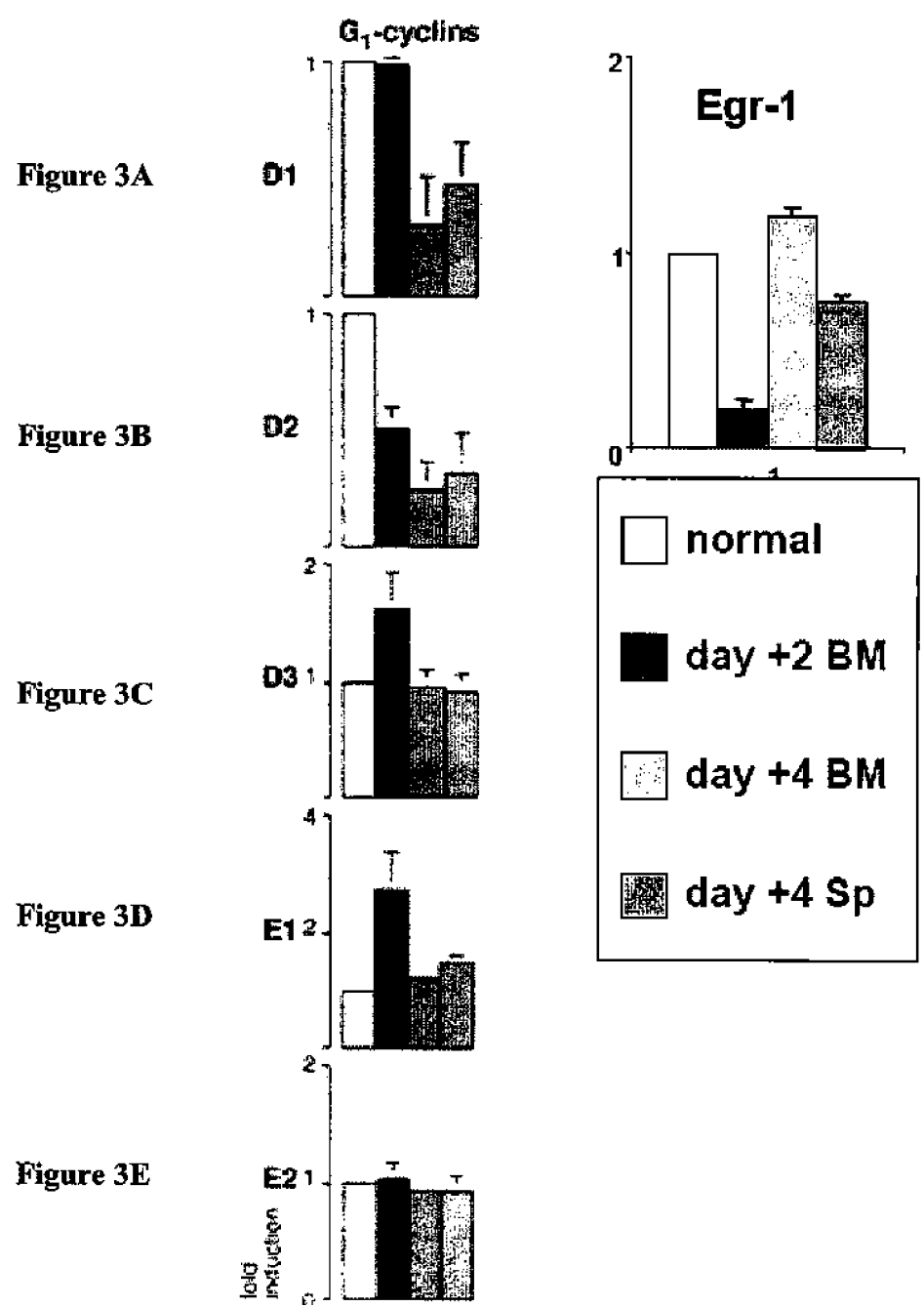

KLS34- gated

KLSF gated

Figure 13B 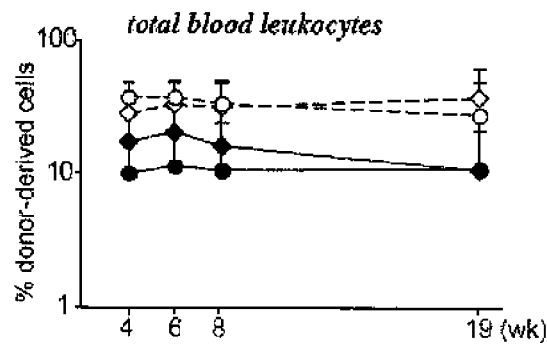 Figure 13C 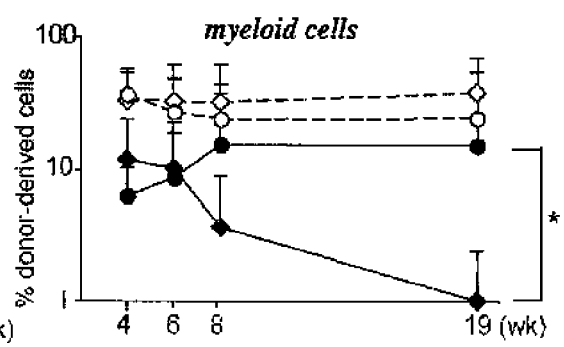
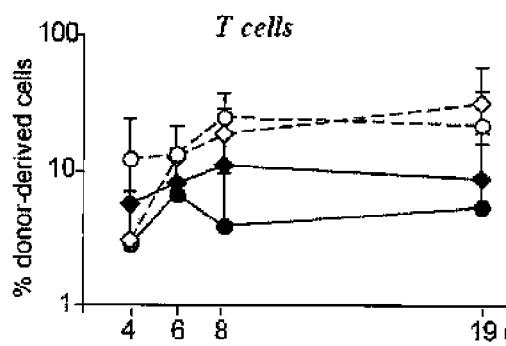
Figure 13D
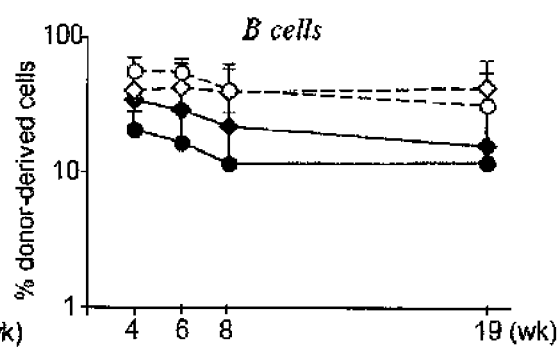
Figure 13E

Figure 17A

```
   1 gcgcagaact tggggagccg ccgccgccat ccgccgccgc agccagcttc cgccgccgca
  61 ggaccggccc ctgccccagc ctccgcagcc gcggcgcgtc cacgcccgcc cgcgcccagg
 121 gcgagtcggg gtcgccgcct gcacgcttct cagtgttccc cgcgccccgc atgtaacccg
 181 gccaggcccc cgcaactgtg tccctgcag ctccagcccc gggctgcacc ccccgcccc
 241 gacaccagct ctccagcctg ctcgtccagg atggccgcgg ccaaggccga gatgcagctg
 301 atgtccccgc tgcagatctc tgacccgttc ggatccttc ctcactcgcc caccatggac
 361 aactacccta agctggagga gatgatgctg ctgagcaacg gggctcccca gttcctcggc
 421 gccgccgggg ccccagaggg cagcggcagc aacagcagca gcagcagcag cggggcggt
 481 ggaggcggcg ggggcggcag caacagcagc agcagcagca gcaccttcaa ccctcaggcg
 541 gacacgggcg agcagcccta cgagcacctg accgcagagt cttttcctga catctctctg
 601 aacaacgaga aggtgctggt ggagaccagt tacccagcc aaaccactcg actgccccc
 661 atcacctata ctggccgctt ttccctggag cctgcaccca acagtggcaa caccttgtgg
 721 cccgagcccc tcttcagctt ggtcagtggc ctagtgagca tgaccaaccc accggcctcc
 781 tcgtcctcag caccatctcc agcggcctcc tccgcctccg cctccagag cccacccctg
 841 agctgcgcag tgccatccaa cgacagcagt cccatttact cagcggcacc caccttcccc
 901 acgccgaaca ctgacatttt ccctgagcca caaagccagg ccttcccggg ctcggcaggg
 961 acagcgctcc agtacccgcc tcctgcctac cctgccgcca agggtggctt ccaggttccc
1021 atgatccccg actacctgtt tccacagcag caggggggatc tgggcctggg cacccccagac
1081 cagaagccct tccagggcct ggagagccgc acccagcagc cttcgctaac ccctctgtct
1141 actattaagg cctttgccac tcagtcgggc tccaggacc tgaaggccct caataccagc
1201 taccagtccc agctcatcaa acccagccgc atgcgcaagt accccaaccg gcccagcaag
1261 acgccccccc acgaacgccc ttacgcttgc ccagtggagt cctgtgatcg ccgcttctcc
1321 cgctccgacg agctcacccg ccacatccgc atccacacag gccagaagcc cttccagtgc
1381 cgcatctgca tgcgcaactt cagccgcagc gaccacctca ccacccacat ccgcacccac
1441 acaggcgaaa agcccttcgc ctgcgacatc tgtggaagaa gtttgccag gagcgatgaa
1501 cgcaagaggc ataccaagat ccacttgcgg cagaaggaca gaaagcaga caaaagtgtt
1561 gtggcctctt cggccacctc ctctctctct tcctacccgt ccccggttgc tacctcttac
1621 ccgtccccgg ttactacctc ttatccatcc ccggccacca cctcatacc atcccctgtg
1681 cccacctcct tctcctctcc cggctcctcg acctacccat ccctgtgca cagtggcttc
1741 ccctcccccgt cggtggccac cacgtactcc tctgttcccc ctgctttccc ggcccaggtc
1801 agcagcttcc cttcctcagc tgtcaccaac tccttcagcg cctccacagg gctttcggac
1861 atgacagcaa ccttttctcc caggacaatt gaaatttgct aaagggaaag gggaaagaaa
1921 gggaaaaggg agaaaaagaa acacaagaga cttaaaggac aggaggagga gatggccata
1981 ggagaggagg gttcctctta ggtcagatgg aggttctcag agccaagtcc tccctctcta
2041 ctggagtgga aggtctattg ccaacaatc ctttctgccc acttcccctt ccccaattac
2101 tattccctt gacttcagct gcctgaaaca gccatgtcca agtcttcac ctctatccaa
2161 agaacttgat ttgcatggat tttggataaa tcatttcagt atcatctcca tcatatgcct
2221 gacccccttgc tcccttcaat gctagaaaat cgagttggca aaatggggtt tgggcccctc
2281 agagccctgc cctgcaccct tgtacagtgt ctgtgccatg gatttcgttt ttcttggggt
2341 actcttgatg tgaagataat ttgcatattc tattgtatta tttggagtta ggtcctcact
2401 tggggaaaa aaaaaaaga aagccaagc aaaccaatgg tgatcctcta ttttgtgatg
2461 atgctgtgac aataagtttg aaccttttt tttgaaacag cagtcccagt attctcagag
2521 catgtgtcag agtgttgttc cgttaacctt tttgtaaata ctgcttgacc gtactctcac
2581 atgtggcaaa atatggtttg gttttcttt tttttttt ttgaaagtgt ttttcttcg
2641 tcctttggt ttaaaaagtt tcacgtcttg gtgccttttg tgtgatgcgc cttgctgatg
2701 gcttgacatg tgcaattgtg agggacatgc tcacctctag ccttaagggg ggcagggagt
2761 gatgatttgg gggaggcttt gggagcaaaa taaggaagag ggctgagctg agcttcggtt
2821 ctccagaatg taagaaaaca aaatctaaaa caaaatctga actctcaaaa gtctattttt
2881 ttaactgaaa atgtaaattt ataatatat tcaggagttg aatgttgta gttacctact
2941 gagtaggcgg cgattttgt atgttatgaa catgcagttc attatttgt ggttctattt
3001 tactttgtac ttgtgtttgc ttaaacaaag tgactgtttg gcttataaac acattgaatg
3061 cgctttattg cccatgggat atgtggtgta tatccttcca aaaaattaaa acgaaaataa
3121 agtagctgcg attggg  (SEQ ID NO:1)
```

Figure 17B

MAAAKAEMQLMSPLQISDPFGSFPHSPTMDNYPKLEEMMLLSNGAPQFLGAAGAPEGSGSNSSSSSGGGG
GGGGGSNSSSSSSTFNPQADTGEQPYEHLTAESFPDISLNNEKVLVETSYPSQTTRLPPITYTGRFSLEPA
PNSGNTLWPEPLFSLVSGLVSMTNPPASSSSAPSPAASSASASQSPPLSCAVPSNDSSPIYSAAPTFPTPN
TDIFPEPQSQAFPGSAGTALQYPPPAYPAAKGGFQVPMIPDYLFPQQQGDLGLGTPDQKPFQGLESRTQQP
SLTPLSTIKAFATQSGSQDLKALNTSYQSQLIKPSRMRKYPNRPSKTPPHERPYACPVESCDRRFSRSDEL
TRHIRIHTGQKPFQCRICMRNFSRSDHLTTHIRTHTGEKPFACDICGRKFARSDERKRHTKIHLRQKDKKA
DKSVVASSATSSLSSYPSPVATSYPSPVTTSYPSPATTSYPSPVPTSFSSPGSSTYPSPVHSGFPSPSVAT
TYSSVPPAFPAQVSSFPSSAVTNSFSASTGLSDMTATFSPRTIEIC (SEQ ID NO:2)

ENHANCING STEM CELL MOBILIZATION

CROSS-REFERENCE TO RELATED APPLICATIONS

This application is the U.S. national stage under 35 USC §371 of International Application Number PCT/US2007/066079, filed on Apr. 5, 2007, which claims the benefit under 35 USC §119(e) to U.S. Provisional Patent Application Ser. No. 60/789,468, filed on Apr. 5, 2006, the entire contents of which are hereby incorporated by reference.

TECHNICAL FIELD

This invention relates to methods and compositions for enhancing hematopoietic stem cell mobilization.

BACKGROUND

Hematopoiesis in adult animals is maintained by a small population of clonogenic, multipotent hematopoietic stem cells (HSC), which maintain throughout life the capacity to self-renew and to differentiate to give rise to progeny cells that ultimately generate all lineages of mature blood cells (Kondo et al., Annu Rev Immunol. 2003; 21:759-806. Epub 2002 December 2017). HSC can be purified from both the bone marrow (BM) and blood of mice by fluorescence activated cell sorting (FACS) according to their unique expression of particular cell surface receptors (e.g., c-kit$^+$, Thy1.1$^{lo}$Lineage marker$^-$, and Sca-1$^+$ (Morrison and Weissman, Immunity. 1994; 1:661-673; Morrison et al., Development. 1997; 124: 1929-1939), abbreviated KTLS, or KLS and Flk-2$^-$ (Christensen and Weissman, Proc Natl Acad Sci USA. 2001; 98:14541-14546. Epub 12001 November 14527), abbreviated KLSF). HSCs can be further divided into long-term hematopoietic stem cells (LTHSC), short-term hematopoietic stem cells (STHSC), and multipotent progenitors (MPP). LTHSC are capable of perpetually repopulating themselves, and also can differentiate into STHSC, which can only repopulate for a finite time period, and non-self renewing MPP.

Upon transplantation, even a single HSC is capable of fully reconstituting hematopoiesis in lethally irradiated recipients, in some cases contributing up to 70% of mature peripheral blood (PB) leukocytes in reconstituted animals (Wagers et al. Science. 2002; 297.2256-2259. Epub 2002 September 2255). This remarkable ability of HSC to functionally regenerate an ablated hematopoietic system forms the basis for bone marrow and PB progenitor cell (PBPC) transplantation, a therapeutic approach that is increasingly employed for the treatment of many diseases, including leukemia and lymphoma (e.g., CML, ALL, AML, and Non-Hodgkin lymphoma), multiple myeloma, breast and ovarian cancers and other solid tumors, bone marrow failure, non-malignant diseases (e.g., aplastic anemia, immune deficiency, and metabolic disorders) and genetic disorders affecting hematopoietic cell function (Weissman, Science. 2000; 287:1442-1446).

In adult mice and humans, the majority of HSC are found in the BM; however, HSC are also constitutively present at low levels in the circulation (see below and Fleming et al., Proc Natl Acad Sci USA. 1993; 90:3760-3764; and Wright et al., Science. 2001; 294:1933-1936). HSCs migrate from the BM to the PB, and likely proliferate in the PB, in a process that is known as "mobilization." Thus, agents that enhance mobilization can either enhance proliferation in the PB, or enhance migration from the SM to the PB, or both. Mobilization may occur to protect against environmental insult, to reconstitute damaged or depleted hematopoietic system, to maintain a fixed number of HSCs in the bone marrow, and possibly for other reasons as well.

The frequency of HSC in the blood can be significantly increased through the use of "mobilizing" agents, including cytotoxic drugs and/or cytokines, which often act to both drive HSC proliferation and to induce HSC migration from the BM into the bloodstream (Papayannopoulou, Ann NY Acad Sci. 1999; 872:187-197; Wright et al., Blood. 2001; 97:2278-2285). In particular, treatment of mice with a combination of cyclophosphamide (Cy) plus granulocyte-colony stimulating factor (GCSF) induces a rapid and reproducible expansion and migration of HSC (see, e.g., Wright et al., Blood. 2001; 97:2278-2285; Neben et al., Blood. 1993; 81:1960-1967; and Morrison et al., Proc Natl Acad Sci USA. 1997; 94:1908-1913). Following administration of Cy plus 2 daily doses of GCSF, the BM HSC population (referred to as day +2 BM HSC) expands dramatically, reaching about 10-12 times the size of the HSC compartment in normal animals (Morrison et al., 1997; supra).

Expansion of HSC in the early phase of mobilization occurs only in the BM (Wright et al., Blood. 2001; 97:2278-2285), but after day +2, HSC frequency in the BM declines, and HSC begin to appear in significant numbers in the blood and spleen of mobilized animals (Morrison et al., 1997, supra). As noted above, HSC numbers in the blood progressively increase throughout Cy/GCSF-treatment. Previous experiments have suggested that the migration of HSC from the BM to the blood and spleen in the context of Cy/GCSF induced mobilization is tightly coordinated with cell cycle, and that mobilized PB (MPB) HSC of Cy/GCSF-treated mice derive from recently divided BM HSC, which transit through the blood from the BM to the spleen (Wright et al., Blood. 2001; 97:2278-2285). However, both the precise mechanisms by which cell cycle progression is regulated in normal and mobilized HSC and the ways in which proliferation may influence the developmental decisions and migratory capacity of these cells remains unclear.

Bone marrow and PBPC transplantation are increasingly common treatment options for hematopoietic and non-hematopoietic cancers, bone marrow dysfunction, and several other metabolic disorders (Kondo et al., 2003, supra). The success of these transplants critically depends on the surprising ability of intravenously infused HSC to accurately and efficiently home to the BM of transplant recipients and, once there, to expand and differentiate to repopulate the peripheral pool of mature blood cells. As such, hematopoietic reconstitution is a multi-step process, and its efficacy may be limited by the ability of transplanted stem cells to (1) migrate to appropriate BM locations, (2) engraft in available BM niches that support HSC survival and function, and/or (3) self-renew and differentiate to both expand the population of HSC and to regenerate peripheral mature blood cells. At present, mechanisms that control HSC movement between IBM and blood, that regulate the BM microenvironment, or that promote the expansion or differentiation of HSC, remain poorly understood. Additional insights into the factors that regulate these crucial decisions are likely to suggest new strategies to improve the efficacy of this approach and reduce transplant-related mortality.

Furthermore, a substantial overlap has been noted in genes that control the normal function of HSC and those that mediate hematopoietic malignancy, implying in particular that neoplastic progenitor cells may exploit the same or similar mechanisms of proliferation and migration as those normally employed by their non-malignant counterparts (Look, Science. 1997; 278:1059-1064; Lecuyer and Hoang, Experimental Hematology, 2004; 32:11-24.). Thus, an improved understanding of the biology and function of normal HSC may ultimately suggest insights into the ways in which these programs are usurped or dysregulated in oncogenesis and cancer metastasis.

SUMMARY

The present invention is based, at least in part, on the discovery that Early Growth Response factor-1 (egr1) regulates both HSC expansion and mobilization processes. Described herein are methods and compositions for modulating these processes by targeting egr1.

Thus, in one aspect, the invention provides methods for increasing the number of hematopoietic stem cells (HSC) in the bone marrow (BM) or peripheral blood (PB) of a subject, by administering to the subject an effective amount of an inhibitor of egr1. The increase in HSC in the BM or PB can be due to enhanced migration, enhanced proliferation, or both. An inhibitor of egr1 can be, e.g., an inhibitory nucleic acid, e.g., an antisense, siRNA, DNAzyme, ribozyme, or competitive inhibitor; a small molecule, e.g., a zinc-finger inhibitor; or a dominant negative form of egr1.

In some embodiments, the methods include administering another HSC mobilizing agent, e.g., an agent selected from the group consisting of interleukin-17 (IL-17), AMD3100, cyclophosphamide (Cy), Docetaxel (DXT), and granulocyte-colony stimulating factor (GCSF).

In some embodiments, the methods described herein include obtaining bone marrow cells or peripheral blood cells from the subject. All or a subset of the BM or PB cells can then be administered to a subject, e.g., the same subject or a second subject, e.g., an HLA type-matched second subject. In some embodiments, the methods also include separating stem cells from the bone marrow or peripheral blood, e.g., using apheresis or leukopheresis. These isolated stem cells can be administered to a subject in need thereof, e.g., the same subject or a second subject, e.g., an HLA type-matched second subject. In some embodiments, the subject in need has a condition selected from the group consisting of cancers and autoimmune disease.

In another aspect, the methods described herein include obtaining bone marrow or peripheral blood from the subject, contacting the BM or PB with an effective amount of an egr1 inhibitor as described herein, e.g., an amount sufficient to increase the number of stem cells in the isolated PB or BM. In some embodiments, the treated PB or BM is then administered to a subject, e.g., the same subject or a second subject, e.g., an HLA type-matched second subject. Optionally, the stem cells can be isolated, enriched or purified, before administration to the subject.

In another aspect, the invention provides methods for identifying a candidate hematopoietic stem cell (HSC) mobilizing agent. The methods include obtaining a sample comprising egr1, e.g., a cell expressing egr1; contacting the sample with a test compound; and measuring an activity of egr1 in the sample, e.g., by assaying egr1 binding to target DNA, or using a reporter gene assay; wherein a test compound that significantly inhibits the activity of egr1 in the sample is a candidate HSC mobilizing agent. In some embodiments, the sample also includes a nucleic acid comprising an egr1 recognition sequence, and the activity is binding of egr1 to the nucleic acid. In some embodiments, the sample further includes a nucleic acid comprising an egr1 recognition sequence operatively linked to a reporter gene, and the activity is egr1-mediated transcription of the reporter gene.

Also provided herein are compositions including (i) an inhibitor of egr1 and (ii) a hematopoietic stem cell (HSC) mobilizing agent. In some embodiments, the inhibitor of egr1 is an inhibitory nucleic acid, e.g., an antisense, siRNA, DNAzyme, ribozyme, or competitive inhibitor; a small molecule zinc-finger inhibitor; or a dominant negative form of egr1. In some embodiments, the HSC mobilizing agent is selected from the group consisting of interleukin-17 (IL-17), AMD3100, cyclophosphamide (Cy), Docetaxel (DXT), and granulocyte-colony stimulating factor (GCSF).

Finally, the invention also includes compositions comprising cells obtained using a method described herein, e.g., BM or PB cells, or stem cells isolated therefrom, that were obtained from a subject treated with an inhibitor of egr1.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIGS. 1A-F illustrate the proliferative activity, as determined by the kinetics of BrdU incorporation, in normal and Cy/G-treated HSC. FIG. 1A is a line graph illustrating % BrdU negative normal BM, day +2 BM, or day +4 BM, Sp, or PB KTLS HSC as determined by flow cytometry after the indicated period of BrdU administration. FIGS. 1B-F are graphs showing the DNA content of KTLS HSC in normal BM (1B), day +2 BM (1C), or day +4 BM (1D), Sp (1E), or PB (1F).

FIG. 2A is a graph illustrating the gating parameters used to sort KTLS or KLSF HSC at distinct stages of the cell cycle (G0, G1, or S/G2/M) before transplant or other manipulation.

FIG. 2B is a bar graph illustrating engraftment of lethally irradiated recipients transplanted with 10 or 50 G0, G1, or S-G2/M KTLS or KLSF HSC cells, sorted as indicated in FIG. 2A. The frequency of recipients showing long-term multilineage reconstitution (LT-MLR) is given for each population.

FIGS. 3A-F are bar graphs illustrating the results of quantitative real time (qRT)-PCR analysis of G1-cyclins (3A-3E) and Egr1 (3F) LANA levels in normal and mobilized KTLS HSC. HSC were sorted from untreated BM (white bars), day +2 BM or day +4 BM or Sp. Results (mean±SD; n=3) have been standardized for β-actin levels and are expressed as percentages of the levels detected in wild-type BM HSC (set to 1).

FIGS. 13B-13E are line graphs showing the results of competitive BM transplantation experiments. 25,000 or 100,000 CD45.2$^+$ or CD45.1$^+$ WBM cells from Egr1$^{+/+}$ (♦ for 25,000 and ◇ for 100,000) or Egr1$^{-/-}$ (● for 25,000, ○ for 100,000) were transplanted into lethally irradiated congenic recipients, along with 200,000 competitor WBM cells. Data are plotted as average % donor-derived total blood leukocytes (13B), Mac 1$^+$Gr1$^+$ myeloid cells (13C), CD3/4/8$^+$ T cells (13D) or B220$^+$ B cells (13E) in each transplantation setting, as determined by flow cytometric analysis of recipient peripheral blood at 4, 6, 8, and 19 weeks post-transplant. Data are compiled from three independent experiments for each transplant assays, with standard deviation indicated.

FIGS. 17A-B are the mRNA (17A, SEQ ID NO:1) and amino acid (17B, SEQ ID NO:2) sequences of human egr-1.

DETAILED DESCRIPTION

Figure 4:
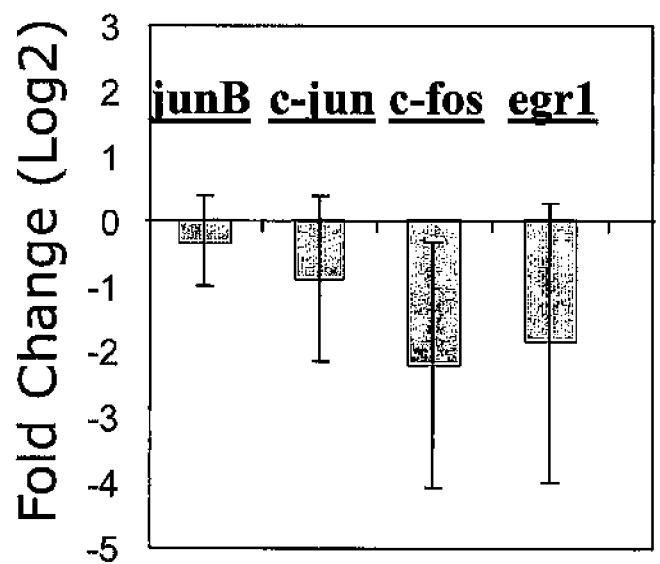
FIG. 4 is a bar graph illustrating the results of cDNA microarray analysis of immediate-early response genes junB, c-jun, c-fos, and egr1 in Day-1 (untreated) vs. Day+2 Cy/G KTLS HSC.

Hematopoietic stem cells (HSC) are capable of generating all lineages of blood and immune cells throughout life due to their capacity to self-renew and to differentiate into descendant blood and immune cells. HSC engraftment and the initiation of hematopoiesis are crucial for the success of bone marrow (BM) transplantation; however, in some patients, the HSCs that can initiate hematopoiesis are limited in abundance. Clinical transplantation often employs treatment with HSC-mobilizing drugs to increase the number of HSCs as well as to promote HSC migration from BM to peripheral blood. Better understanding of the underlying molecular mechanisms of HSC self-renewal and mobilization will be essential to the improved success of clinical transplantation.

Using cDNA microarray analyses to identify molecular mediators involved in HSC expansion and migration, early growth response factor (Egr)-1 was found to be strongly repressed during the proliferative phase of HSC mobilization. Egr1 is a zinc-finger transcription factor, and has been shown to play various roles in cell growth, development, death, and cell cycle control in many different types of cells. However, a potential involvement of Egr1 in HSC biology has not been previously described. As described herein, absence of Egr1 leads to an increase in the size of the HSC pool and a tendency toward increased HSC proliferation. Interestingly, in Egr1 deficient mice, a substantial population of HSCs is found in the peripheral blood, indicative of constitutive HSC mobilization. These studies suggest that egr1 coordinately regulates HSC self-renewal and mobilization pathways, and that inhibiting egr1 is useful in increasing HSC mobilization to the peripheral blood.

Early Growth Response Factor-1 (egr1)

Egr1 is a zinc-finger transcription factor that has variously been referred to as Zif268, Krox 24, TIS8, and NGFI-A; see, e.g., Sukhatme et al., Cell. 1988; 53:3743; Christy et al., Proc. Natl. Acad. Sci. USA 1988; 85:7857-7861; Lemaire et al, Proc. Nat. Acad. Sci. 1988; 85:4691-4695; Milbrandt, Science. 1987; 238(4828):797-9; Lim et al., Oncogene. 1987: 1(3):263-270. Egr1 binds with high affinity to the DNA sequences 5'-TGCG(T/g)(G/A)GG(C/a/t)GG-3' (SEQ ID NO:3) (Swirnoff and Milbrandt, Mol Cell Biol. 1995; 15(4): 2275-87; lower case letters indicate bases selected less frequently), e.g., 5'-GCG(G/T)GGGCG'3' (SEQ BD NO:4) (Christy and Nathans, Proc. Natl. Acad. Sci. USA, 1989, 86:8737-8741; Cao et al., J. Biol. Chem., 1993, 271:18576-18581). It is an immediate early response gene that is inducible by mitogenic stimulation, UV/gamma-ray irradiation, and/or oxidative stress or shear stress (Thiel and Cibelli, J. Cell. Physiol. 2002; 193:287-292). Egr1 has been thought to control cell cycle reentry, and also plays other biological roles in development, cell growth, cell survival, wound healing and inflammation (Thiel and Cibelli, J. Cell. Physiol. 2002; 193: 287-292). Egr1$^{-/-}$ mice develop normally, but increasing evidence indicates that Egr1$^{-/-}$ mice may be less protected against stress and environmental insult (Khachigian and Collins, Circ. Res. 1997; 81:457-461; Yan et al., Proc. Natl. Acad. Sci. U.S.A. 1998; 95:8298-8303; Khachigian et al., Science, 1996, 271:1427-1431; Santiago et al., Am. J. Pathol., 1999, 154:937-944). Egr1 can act as both a tumor suppressor and a tumor promoter (Thiel and Cibelli, J. Cell. Physiol. 2002; 193:287-292; Abdulkadir et al., Hum. Pathol. 32(9):935-9 (2001); Abdulkadir et al., Nat. Med. 7(1):101-7 (2001); Huang et al., Cancer Res. 1995 Nov. 1; 55(21):5054-62 (1995); Clin. Cancer Res. 2001 September; 7(9):2788-96 (2001); Erratum in: Clin. Cancer Res. 8(1):299 (2002). Downstream target genes of egr1 include p53, p19, PTEN, Tgf-β, PDGF A/B, c-jun, ICAM-1, M-CSF, TNF-α, VEGF, MMP1, Cyclin D1, D2, and Fas (Krones-Herzig et al., Proc. Natl. Acad. Sci. U.S.A. 100(6):3233-8 (2003); Virolle et al., J. Biol. Chem. 2003; 278(14):11802-10 (2003); Liu et al., J. Biol. Chem. 1998; 5(1); 3-28; Hass et al., J. Biol. Chem. 1999; 274:679-85; Vidal et al., Blood, 2000; 95:3387-95). The role of egr1 in hematopoietic cell development has been the subject of previous research, see, e.g., Bettini et al., JEM, 2002, 169(4):1713-1720; Carleton et al., J. Immunol., 2002, 168(4):1649-58; Haks et al., Immunity, 2005, 22(5):595-606; Richards et al., J. Immunol., 2001, 166(6):3855-64; Dinkel et al., J. Exp. Med., 1998, 188 (12):2215-24; and Krishnaraju et al., Blood, 2001, 97(5):1298-30; Nguyen et al., Cell, 1993, 72(2):197-209; Lee et al., Mol Cell Biol., 1996, 16(8):4566-72. The sequence of human egr1 protein is available in the GenBank database at Accession No. NP_001955.1; the mRNA is at Accession No. NM_001964.2. Additional information regarding egr1 can be found on the internet at ncbi.nlm.nih.gov, in the UniGene database at UniGene Hs.326035, and in the Entrez Gene database at GeneID: 1958.

Active fragments of egr1 include those portions of the protein that bind DNA, e.g., one or more of the two C2H2 type DNA-binding zinc fingers (see, e.g., Sukhatme et al., 1988, supra), e.g., amino acids 338-362 and/or 368-390 of GenBank Acc. No. NP_001955.1. Exemplary active fragments are described in Huang et al., Cancer Res. 1995; 55(21):5054-5062, and in Jain et al., J. Biol. Chem. 1996; 271(23)-13530-6.

Inhibitors of egr1

As used herein, an inhibitor of egr1 is a direct and specific inhibitor of egr1, i.e., an agent that acts directly on the egr1 protein or nucleic acid, e.g., to decrease egr1 protein activity or levels, to decrease egr1 mRNA levels, or to decrease egr1 transcription or translation. Such inhibitors have the end effect of reducing egr1 transcription factor activity levels in a cell. A number of inhibitors of egr1 are known in the art, as are methods of identifying new ones. General classes of inhibitors of egr1 include, but are not limited to, inhibitory nucleic acids, e.g., oligonucleotides containing the egr1 binding site, siRNA, antisense, DNAzymes, and ribozymes; small organic or inorganic molecules, e.g., zinc finger inhibitors; peptides, e.g., peptides that bind egr1; proteins, e.g., dominant negatives of egr1, e.g., pBX-EGRΔNH$_2$ (see, e.g., Dieckgraefe and Weems, Am. J. Physiol. Gastrointest. Liver Physiol. 1999; 276:G322-G330; see also Al-Sarraj et al., J. Cell. Biochem. 2005; 94(1):153-67; Levkovitz and Baraban, J. Neurosci. 2001; 21(16):5893-901; and Levkovitz and Baraban, J. Neurosci. 2002; 22(10):3845-54, Russo et al., Proc. Natl. Acad. Sci. U. S. A., 1995, 92:6873-6877; Carman and Monroe, DNA Cell Biol., 1995, 14:581); Madden et al., Science, 1991, 253:1550-1553. An inhibitor that acts directly on egr1, for example, can affect binding of egr1 to its target nucleic acid (Carman and Monroe, DNA Cell Biol., 1995, 14:581; Madden et al., Science, 1991, 253:1550-1553), can affect interactions of egr1 with one or more cooperating transcription factors, coactivators or corepressors such as Nab1 (Russo et al., Proc. Natl. Acad. Sci. U.S.A., 1995, 92:6873-6877), can sequester egr1 away from the cytoplasm, can induce the degradation of egr1 protein or mRNA, can impair egr1 transcription and/or translation.

A number of egr1 inhibitors are known in the art, see, e.g., Muthukkumar et al., J. Biol. Chem. 1997; 272(44):27987-93 (describing a phosphorothioate-capped antisense Egr1 oligodeoxynucleotide (ODN) with the sequence 5-GsCsGGGGTGCAGGGGCACAsCsT-3 (SEQ ID NO:5); Okada et al., FASEB J. 2001; 15:2757-2759 (phosphorothioate antisense oligodeoxyribonucleotide with the sequence 3'-TAC-CGTCGCCGGTTC-5' (SEQ ID NO:6); Lowe et al., Thromb. Haemost. 2002; 87(1):134-40 (catalytic ODN); Fahmy and Khachigian, Nuc. Acids Res. 2004; 32(7):2281-2285 (locked nucleic acid modified DNA enzymes, also known as DNAzymes); Santiago et al., Nat. Med. 1999; 11: 1264-1269, Lowe et al., Thromb. Haemost. 2002; 87:134-140, and Lowe et al., Circ. Res. 2001; 89:670-677 (DNAzymes targeting egr1); Malkani et al., Learn Mem. 2004; 11(5):617-24. Erratum in: Learn Mem. 2004; 11(6):797 (antisense-ODN with the sequence 5'-GGTAGTTGTCCATGGTGG-3' (SEQ ID NO:7); and Pinsky et al., U.S. Pat. No. 6,969,704 (describing a competitive inhibitor with the sequence

```
5'-CTTGGCCGCTGCCAT-3'.      (SEQ ID NO: 8))
```

Inhibitors of zinc finger proteins can also be used. Zinc finger inhibitors can work by, e.g., disrupting the zing finger by modification of one or more cysteines in the binding sites for $Zn^{2+}$ in the zinc finger protein, resulting in the ejection of zinc ion; removing the zinc from the zinc finger moiety, e.g., by specific chelating agents, also known as "zinc ejectors", including azodicarbonamide (ADA); or forming a ternary complex at the site of zinc binding on zinc finger proteins, resulting in inhibition of the DNA or RNA binding activity of zinc finger proteins. A number of small molecule inhibitors of zinc fingers are known in the art. For example, picolinic acid derivatives such as a small molecule called Picolinic acid drug substance (PCL-016), and a derivative thereof FSR-488, see, e.g., U.S. Pat. App. Pub. No. 2005/0239723, available from Novactyl (St. Louis, Mo.). U.S. Pat. No. 6,410,570 describes other picolinc acid derivatives with zinc-binding capabilities.

Another suitable egr1 inhibitor is the "TF decoy," a double stranded nucleic acid that blocks the DNA binding of transcription factors, including zinc finger proteins. Cis element double-stranded (decoy) oligonucleotides scavenge active transcription factors, thereby blocking their binding to the promoter regions in target genes. Egr1 decoy and mutated controls have been described previously, see, e.g., Kamimura et al., Hypertension 44(6):944-951 (2004). Their sequences were as follows: Egr1 consensus sequence, (5'-GGATC-CAGCGGOGGCGAGCGGGGGCGA-3'; SEQ ID NO:9); and mutated control (5'-GGATCCAGCTAGGGC-GAGCTAGGGCGA-3'; SEQ ID NO:10.

In some embodiments, e.g., where the egr1 inhibitor is a protein or peptide or could otherwise benefit from delivery into the cell the inhibitor includes a cell-penetrating peptide sequence that facilitates delivery of the inhibitor to the intracellular space, e.g., HIV-derived TAT peptide, penetratins, transportans, or hCT derived cell-penetrating peptides, see, e.g., Caron et al., (2001) Mol Ther 3(3):310-8; Langel, Cell-Penetrating Peptides: Processes and Applications (CRC Press, Boca Raton Fla. 2002); El-Andaloussi et al., (2005) Curr Pharm Des. 11(28):3597-611; and Deshayes et al., (2005) Cell Mol Life Sci. 62(16):1839-49.

siRNA Molecules

RNAi is a process whereby double-stranded RNA (dsRNA, also referred to herein as si RNAs or ds siRNAs, for double-stranded small interfering RNAs,) induces the sequence-specific degradation of homologous mRNA in animals and plant cells (Hutvagner and Zamore, Curr. Opin. Genet. Dev.: 12, 225-232 (2002); Sharp, Genes Dev., 15:485-490 (2001)). In mammalian cells, RNAi can be triggered by duplexes of small interfering RNA (siRNA) (Chiu et al., Mol. Cell. 10:549-561 (2002); Elbashir et al., Nature 411:494-498 (2001)), or by micro-RNAs (miRNA), functional small-hairpin RNA (shRNA), or other dsRNAs which are expressed in vivo using DNA templates with RNA polymerase III promoters (Zeng et al., Mol. Cell 9:1327-1333 (2002); Paddison et al., Genes Dev. 16:948-958 (2002); Lee et al., Nature Biotechnol, 20:500-505 (2002); Paul et al., Nature Biotechnol. 20:505-508 (2002); Tuschl, T., Nature Biotechnol. 20:440-448 (2002); Yu et al., Proc. Natl. Acad. Sci. USA 99(9):6047-6052 (2002); McManus et al., RNA 8:842-850 (2002); Sui et al., Proc. Natl. Acad. Sci. USA 99(6):5515-5520 (2002)).

The nucleic acid molecules or constructs can include dsRNA molecules comprising 16-30, e.g., 16, 17, 18, 19, 20, 21, 22, 23, 24, 25, 26, 27, 28, 29, or 30 nucleotides in each strand, wherein one of the strands is substantially identical, e.g., at least 80% (or more, e.g., 85%, 90%, 95%, or 100%) identical, e.g., having 3, 2, 1, or 0 mismatched nucleotide(s), to a target region in the mRNA, and the other strand is complementary to the first strand. The dsRNA molecules can be chemically synthesized, or can transcribed be in vitro from a DNA template, or in vivo from, e.g., shRNA. The dsRNA molecules can be designed using any method known in the art; a number of algorithms are known, and are commercially available. Gene walk methods can be used to select siRNA with optimized inhibitory activity.

The nucleic acid compositions can include both siRNA and modified siRNA derivatives, e.g., siRNAs modified to alter a property such as the pharmacokinetics of the composition, for example, to increase half-life in the body, as well as engineered RNAi precursors.

siRNAs can be delivered into cells by methods known in the art, e.g., cationic liposome transfection and electroporation. siRNA duplexes can be expressed within cells from engineered RNAi precursors, e.g., recombinant DNA constructs using mammalian Pol III promoter systems (e.g., H1 or U6/snRNA promoter systems (Tuschl (2002), supra) capable of expressing functional double-stranded siRNAs; (Bagella et al., J. Cell. Physiol. 177:206-213 (1998); Lee et al. (2002), supra; Miyagishi et al. (2002), supra; Paul et al. (2002), supra; Yu et al. (2002), supra; Sui et al. (2002), supra). Transcriptional termination by RNA Pol III occurs at runs of four consecutive T residues in the DNA template, providing a mechanism to end the siRNA transcript at a specific sequence. The siRNA is complementary to the sequence of the target gene in 5'-3' and 3'-5' orientations, and the two strands of the siRNA can be expressed in the same construct or in separate constructs. Hairpin siRNAs, driven by H1 or U6 snRNA promoter and expressed in cells, can inhibit target gene expression (Bagella et al. (1998), supra; Lee et al. (2002), supra; Miyagishi et al. (2002), supra; Paul et al. (2002), supra; Yu et al. (2002), supra; Sui et al. (2002) supra). Constructs containing siRNA sequence under the control of T7 promoter also make functional siRNAs when cotransfected into the cells with a vector expression T7 RNA polymerase (Jacque (2002), supra).

RNAi against egr1 is described in Stuart et al., 2005, Oncogene, 24(55):8085-92 (2005), and Cron et al., 2006, J. Immunol, 176:811-818).

Vectors for producing siRNAs targeting egr1 are commercially available, see, e.g., the GenEclipse™ EGR1 Vector-based RNAi Kit (Chemicon, Temecula, Calif.).

Antisense

An "antisense" nucleic acid can include a nucleotide sequence that is complementary to a "sense" nucleic acid encoding a protein, e.g., complementary to the coding strand of a double-stranded cDNA molecule or complementary to an egr1 mRNA sequence. The antisense nucleic acid can be complementary to an entire coding strand of a target sequence, or to only a portion thereof. In another embodiment, the antisense nucleic acid molecule is antisense to a "noncoding region" of the coding strand of a nucleotide sequence (e.g., the 5' and 3' untranslated regions).

An antisense nucleic acid can be designed such that it is complementary to the entire coding region of a target mRNA, but can also be an oligonucleotide that is antisense to only a portion of the coding or noncoding region of the target mRNA. For example, the antisense oligonucleotide can be complementary to the region surrounding the translation start site of the target mRNA, e.g., between the −10 and +10 regions of the target gene nucleotide sequence of interest. An antisense oligonucleotide can be, for example, about 7, 10, 15, 20, 25, 30, 35, 40, 45, 50, 55, 60, 65, 70, 75, 80, or more nucleotides in length.

An antisense nucleic acid can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. The antisense nucleic acid also can be produced biologically using an expression vector into which a nucleic acid has been subcloned in an antisense orientation (i.e., RNA transcribed from the inserted nucleic acid will be of an antisense orientation to a target nucleic acid of interest, described finer in the following subsection).

Based upon the sequences disclosed herein, one of skill in the art can easily choose and synthesize any of a number of appropriate antisense molecules for use in accordance with the present invention. For example, a "gene walk" comprising a series of oligonucleotides of 15-30 nucleotides spanning the length of a target nucleic acid can be prepared, followed by testing for inhibition of target gene expression. Optionally, gaps of 5-10 nucleotides can be left between the oligonucleotides to reduce the number of oligonucleotides synthesized and tested.

In some embodiments, the antisense nucleic acid molecule is an α-anomeric nucleic acid molecule. An α-anomeric nucleic acid molecule forms specific double-stranded hybrids with complementary RNA in which, contrary to the usual β-units, the strands run parallel to each other (Gaultier et al., Nucleic Acids. Res. 15:6625-6641 (1987)). The antisense nucleic acid molecule can also comprise a 2'-o-methylribonucleotide (Inoue et al. Nucleic Acids Res. 15:6131-6148 (1987)) or a chimeric RNA-DNA analogue (Inoue et al. FEBS Let., 215.327-330 (1987)).

In some embodiments, the antisense nucleic acid is a morpholino oligonucleotide (see, e.g., Heasman, Dev. Biol. 243: 209-14 (2002); Iversen, Curr. Opin. Mol. Ther. 3:235-8 (2001); Summerton, Biochim. Biophys. Acta. 1489:141-58 (1999).

Target gene expression can be inhibited by targeting nucleotide sequences complementary to a regulatory region (e.g., promoters and/or enhancers) to form triple helical structures that prevent transcription of the Spt5 gene in target cells. See generally, Helene, *Anticancer Drug Des.* 6:569-84 (1991); Helene, *Ann. N.Y. Acad. Sci.* 660:27-36 (1992); and Maher, *Bioassays* 14:807-15 (1992). The potential sequences that can be targeted for triple helix formation can be increased by creating a so called "switchback" nucleic acid molecule. Switchback molecules are synthesized in an alternating 5'-3', 3'-5' manner, such that they base pair with first one strand of a duplex and then the other, eliminating the necessity for a sizeable stretch of either purines or pyrimidines to be present on one strand of a duplex.

Antisense molecules targeting egr1 are known in the art, see, e.g., Malkani et al., Learn. Mem. 11:617624 (2004), which described antisense oligos with the sequence 5'-GG-TAGTTGTCCATGGTGTG-3' (SEQ ID NO:11), and a scrambled control oligo (5'-GTTGGAGTCGGTGGTTCA-3'; SEQ ID NO:12)). Egr1 antisense molecules with the sequence 5'-GCGGGGTGCAGGGGCACACT-3' (SEQ ID NO:13) were described in Banks et al., J. Appl. Physiol. 98:732-738 (2005). See also Virolle et al., Nat. Cell Biol. 3, 1124-1128 (2001).

Ribozymes/DNAzymes

Ribozymes are catalytic RNA molecules that can be engineered to enzymatically cleave and inactivate other RNA targets in a specific, sequence-dependent fashion. DNAzymes are catalytic DNA molecules that can be engineered to act in the same way, but are more stable and in some cases more effective than RNAzymes. By cleaving the target RNA, these catalytic nucleic acid molecules inhibit translation, thus preventing the expression of the target gene. They can be chemically synthesized in the laboratory and structurally modified to increase their stability and catalytic activity using methods known in the art. Alternatively, ribozyme or DNAzyme genes can be introduced into cells through gene-delivery mechanisms known in the art.

A ribozyme or DNAzyme having specificity for a target nucleic acid can include one or more sequences complementary to the nucleotide sequence of egr1, and a sequence having known catalytic sequence responsible for mRNA cleavage (see U.S. Pat. No. 5,093,246 or Haselhoff and Gerlach Nature 334:585-591 (1988)). For example, a derivative of a Tetrahymena L-19 IVS RNA can be constructed in which the nucleotide sequence of the active site is complementary to the nucleotide sequence to be cleaved in a target egr1 mRNA. See, e.g., Cech et al. U.S. Pat. No. 4,987,071; and Cech et al. U.S. Pat. No. 5,116,742. Alternatively, a target mRNA can be used to select a catalytic RNA having a specific ribonuclease activity from a pool of RNA molecules. See, e.g., Bartel and Szostak, Science 261:1411-1418 (1993). For a general review of DNAzymes, see Khachigian, Curr. Op. Mol. Ther. 2002; 4(2):119-121.

DNAzymes targeting egr1 have been successfully used, and are described in Fahmy and Khachigian, Nuc. Acids Res. 2004; 32(7):2281-2285; Santiago et al., Nat. Med. 1999; 11: 1264-1269; and Lowe et al., Thromb. Haemost. 2002; 87:134-140. For example, a DNAzyme named DzF that targeted egr1 with the sequence 5'-GCGGGGACAGGCTAGC-TACAACGACAGCTGCATTi-3' (SEQ ID NO 14) was described in Lowe et al., Circ. Res. 2001; 89:670-677; see also Mitchell et al., Nuc. Ac. Res. 2004; 32(10):3065-3069.

Pharmaceutical Compositions

The methods described herein include the manufacture and use of pharmaceutical compositions, which include compounds identified by a method described herein as active ingredients. Also included are the pharmaceutical compositions themselves.

Pharmaceutical compositions typically include a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions, e.g., mobilizing agents including growth factors such as G-CSF.

Pharmaceutical compositions are typically formulated to be compatible with the intended route of administration. Examples of routes of administration include parenteral, e.g., intravenous, intradermal, subcutaneous, oral (e.g., inhalation), transdermal (topical), transmucosal, and rectal administration. Methods of formulating suitable pharmaceutical compositions are known in the art, see, e.g., the books in the series *Drugs and the Pharmaceutical Sciences: a Series of Textbooks and Monographs* (Dekker, NY).

In some embodiments, the pharmaceutical compositions are formulated to target delivery of the active agent to the bone marrow. For example, in some embodiments, the active agent is formulated in liposomes, which can effect more targeted delivery to the BM while reducing side effects. See, e.g., Hassan et al., Bone Marrow Transplant. 1998; 22(9): 913-8; Zou et al., Clin Cancer Res. 1995; 1(11): 1369-74; Mascarenhas et al., Blood. 1998; 92(10):3537-45. Myeloid-specific antigens can also be used to target the BM; see, e.g., Orchard and Cooper, Q. J. Nucl. Med. Mol. Imaging. 2004; 48(4):267-78.

In some embodiments, the invention includes compositions including (i) an inhibitor of egr1, as described herein, and (ii) a hematopoietic stem cell (HSC) mobilizing agent.

Inhibitors of egr1 include, but are not limited to, nucleic acids, e.g., an antisense, siRNA, DNAzyme, ribozyme, TF decoys, or competitive inhibitors; small molecules, e.g., small molecule zinc-finger inhibitors; and dominant negative forms of egr1.

HSC mobilizing agents include interleukin-17 (IL-17; Journal of Immunol. 2001; 167: 2081-2086), AMD3100 (Flomenberg et al., Acta Haematol. 2005; 114(4):198-205), cyclophosphamide (Cy), Docetaxel (DXT; Ojeifo et al., Experimental Hematology 2000; 28:451-459), and granulocyte-colony stimulating factor (GCSF).

The pharmaceutical compositions can be included in a container, pack, or dispenser together with instructions for administration.

Methods of Treatment

The methods described herein include methods for the treatment of subjects who are in need of increased numbers of stem cells. In some embodiments, the subject is scheduled to or intends to donate stem cells, e.g., for use in heterologous or autologous transplantation. Generally, the methods include administering a therapeutically effective amount of therapeutic compound as described herein, to a subject who is in need of, or who has been determined to be in need of, such treatment. Administration of a therapeutically effective amount of a composition described herein for the treatment of such subjects will result in an increased number and/or frequency of HSC, e.g., LTHSC, e.g., in the PB. In some embodiments, such administration will result in an increase of about 10-500-fold in the number of HSC in the PB. Methods of measuring such increases are known in the art, see, e.g., Neben et al., Blood. 1993; 81(7):1960-7; Ashihara et al. Exp. Hematol. 2000; 28(3):311-7; Pruijt et al., Proc. Natl. Acad. Sci. U.S.A. 1999; 96(19):10863-8.

Dosage, toxicity and therapeutic efficacy of the compounds can be determined by standard pharmaceutical procedures, e.g., in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

An "effective amount" is an amount sufficient to effect a significant increase in the number and/or frequency of HSC, e.g., LTHSC, in the PB. An effective amount can be administered in one or more administrations, applications or dosages. A therapeutically effective amount of a composition depends on the composition selected. The compositions can be administered one from one or more times per day to one or more times per week; including once every other day. The skilled artisan will appreciate that certain factors may influence the dosage and timing required to effectively treat a subject, including but not limited to previous treatments, the general health and/or age of the subject, and other diseases present. Moreover, treatment of a subject with a therapeutically effective amount of the compositions described herein can include a single treatment or a series of treatments.

In some embodiments, the methods of treatment described herein include administering another HSC mobilizing agent, e.g., an agent selected from the group consisting of, but not limited to, interleukin-17 (IL-17; Journal of Immunol. 2001; 167: 2081-2086), AMD3100 (Flomenberg et al., Acta Haematol. 2005; 114(4):198-205), cyclophosphamide (Cy), Docetaxel (DXT; Ojeifo et al., Experimental Hematology 2000; 28:451-459), and granulocyte-colony stimulating factor (GCSF).

In some embodiments, once PB or BM is obtained from a subject who has been treated using an egr1 inhibitor as described herein, the stem cells can be isolated therefrom, e.g., using a standard method such as apheresis or leukapheresis.

In some embodiments, the methods described herein further include obtaining a BM or PB from an untreated subject, using standard methods. Once the BM or PB is obtained, it is maintained in vitro and contacted with an effective amount of an inhibitor of egr1 as described herein. In this context, an effective amount is an amount sufficient to increase numbers of stem cells in the BM or PB. At that point, the egr1 inhibitor can be removed, and the PB or BM can be reintroduced into the subject, or transplanted into a second subject, e.g., an HLA-matched subject. In some embodiments, the stem cells can be isolated therefrom, e.g., substantially purified, using a standard method such as apheresis or leukapheresis, and only the stem cells are transplanted or reintroduced.

In some embodiments, the methods include administering the isolated stem cells to a subject, e.g., reintroducing the cells into the same subject or transplanting the cells into a second subject, e.g., an HLA type-matched second subject.

Subjects that can usefully be treated using the stem cells, PB or BM include any subjects who can be normally treated with a bone marrow or stem cell transplant, e.g, subjects who have cancers, e.g., neuroblastoma (cancer that arises in immature nerve cells and affects mostly infants and children), myelodysplasia, myelofibrosis, breast cancer, renal cell carcinoma, or multiple myeloma. For example, the cells can be transplanted into subjects who have cancers that are resistant to treatment with radiation therapy or chemotherapy, e.g., to restore stem cells that were destroyed by high doses of chemotherapy and/or radiation therapy used to treat the cancers.

In some embodiments, the subject has a hematopoietic neoplastic disorder. As used herein, the term "hematopoietic neoplastic disorders" includes diseases involving hyperplastic/neoplastic cells of hematopoietic origin, e.g., arising from myeloid, lymphoid or erythroid lineages, or precursor cells thereof. In some embodiments, the diseases arise from poorly differentiated acute leukemias, e.g., erythroblastic leukemia and acute megakaryoblastic leukemia. Additional exemplary myeloid disorders include, but are not limited to, acute promyeloid leukemia (APML), acute myelogenous leukemia (AML) and chronic myelogenous leukemia (CML) (reviewed in Vaickus, L. (1991) Crit Rev. in Oncol./Hemotol. 11:267-97); lymphoid malignancies include, but are not limited to acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to Hodgkin's Disease and Medium/High grade (aggressive) Non-Hodgkin's lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease. In general, the methods will include administering the PB, BM, or stem cells to restore stem cells that were destroyed by high doses of chemotherapy and/or radiation therapy, e.g., therapy used to treat the disorders.

In some embodiments, the BM, PB or stem cells are used to treat a subject who has an autoimmune disease, e.g., multiple sclerosis (MS), myasthenia gravis, autoimmune neuropathy, scleroderma, aplastic anemia, and systemic lupus erytematosus In some embodiments, the subject who is treated has a non-malignant disorder such as aplastic anemia, a hemoglobinopathy, including sickle cell anemia, or an immune deficiency disorder.

Methods of Screening

The invention includes methods for screening of test compounds, to identify compounds that inhibit egr1. In general, the methods will include providing a sample comprising egr1 or an active fragment thereof; contacting the sample with one or more test compounds; and evaluating an effect of the compound on an activity of egr1 in the sample. In some embodiments, the methods include a competitive binding experiment, e.g., the sample includes a fragment of DNA, e.g., a fragment comprising an egr1 binding sequence, e.g., TGCG(T/g)(G/A)GG(C/a/t)GG (SEQ ID NO:3), GCG(G/T)GGGCG (SEQ ID NO:4), TGCGGGGGGCG (SEQ ID NO:15), or TCCTCCTCCTCC (SEQ ID NO:16), and the methods include determining whether the test compound affects binding of egr1 to the DNA. A number of methods are known in the art for detecting binding. For example, either the DNA fragment or the egr1 can be attached to a surface (e.g., a bead or slide), and the other of the DNA fragment or egr1 is labeled (e.g., radioactively or with a fluorophore). Binding of the DNA fragment to the egr1 is then detected, e.g., in the presence and absence of a test compound, by detecting the label.

In some embodiments, the method includes determining whether the test compound affects egr1-mediated transcription. Thus, the sample can include an egr1 recognition sequence operatively linked to a reporter gene, such as a fluorescent protein (e.g., GFP, or a variant thereof) or other detectable gene product (e.g., a protein that participates in a colorimetric reaction, e.g., LacZ). The effect of the test compound on egr1-mediated transcription of the reporter gene can be measured by detecting expression of the reporter gene, e.g., by detecting fluorescent emission in the case of a fluorescent protein.

In some embodiments, the test compounds are initially members of a library, e.g., an inorganic or organic chemical library, peptide library, oligonucleotide library, or mixed-molecule library. In some embodiments, the methods include screening small molecules, e.g., natural products or members of a combinatorial chemistry library. As used herein, "small molecules" refers to small organic or inorganic molecules of molecular weight below about 3,000 Daltons.

A given library can comprise a set of structurally related or unrelated test compounds. Preferably, a set of diverse molecules should be used to cover a variety of functions such as charge, aromaticity, hydrogen bonding, flexibility, size, length of side chain, hydrophobicity, and rigidity. Combinatorial techniques suitable for creating libraries are known in the art, e.g., methods for synthesizing libraries of small molecules, e.g., as exemplified by Obrecht and Villalgordo, *Solid-Supported Combinatorial and Parallel Synthesis of Small-Molecular-Weight Compound Libraries*, Pergamon-Elsevier Science Limited (1998). Such methods include the "split and pool" or "parallel" synthesis techniques, solid-phase and solution-phase techniques, and encoding techniques (see, for example, Czarnik, Curr. Opin. Chem. Bio. 1:60-6 (1997)). In addition, a number of libraries, including small molecule libraries, are commercially available.

In some embodiments, the test compounds are peptide or peptidomimetic molecules, e.g., peptide analogs including peptides comprising non-naturally occurring amino acids or having non-peptide linkages; peptidomimetics (e.g., peptoid oligomers, e.g., peptoid amide or ester analogues, β-peptides, D-peptides, L-peptides, oligourea or oligocarbamate); small peptides (e.g., pentapeptides, hexapeptides, heptapeptides, octapeptides, nonapeptides, decapeptides, or larger, e.g., 20-mers or more); cyclic peptides; other non-natural or unnatural peptide-like structures; and inorganic molecules (e.g., heterocyclic ring molecules). In some embodiments, the test compounds are nucleic acids, e.g., DNA or RNA oligonucleotides, or DNAzymes (DNA-based enzymes, cation-dependent enzymatic molecules composed entirely of DNA that can be engineered to cleave target mRNA in a gene-specific and catalytically efficient manner. In some embodiments, the test compounds include viral vectors for the delivery of such nucleic acids. In some embodiments, the test compounds are known or suspected zinc-finger inhibitors.

The libraries useful in the methods of the invention can include the types of compounds that will potentially bind to egr1. For example, where egr1 has a known protein binding partner, the test compounds can be structurally similar to the known binding partner. As one example, in a method where egr1 or an active fragment thereof (e.g., a DNA-binding fragment) is used to screen a library for test compounds that bind to the DNA binding site of egr1, the test compounds can be peptides or peptidomimetics that are structurally similar to the natural nucleic acid sequence that binds egr1, i.e., TGCG (T/g)(G/A)GG(C/a/t)GG (SEQ ID NO:3), GCG(G/T)GGGCG (SEQ ID NO:4), TGCGGGGCG (SEQ ID NO:15), or TCCTCCTCCTCC (SEQ ID NO:16).

In some embodiments, test compounds and libraries thereof can be obtained by systematically altering the structure of a first test compound. Taking a small molecule as an example, e.g., a first small molecule is selected that is structurally similar to a known natural binding partner of egr1 (e.g., an oligonucleotide comprising the nucleic acid sequence TGCG(T/g)(G/A)GG(C/a/t)GG (SEQ ID NO:3), GCG(G/T)GGGCG (SEQ ID NO:4), TGCGGGGCG (SEQ ID NO:15), or TCCTCCTCCTCC (SEQ ID NO:16)), or has been identified as capable of binding and/or inhibiting egr1. For example, in one embodiment, a general library of small molecules is screened, e.g., using the methods described herein, to select a fist test small molecule. Using methods known in the art, the structure of that small molecule is identified if necessary and correlated to a resulting biological activity, e.g., by a structure-activity relationship study. As one of skill in the art will appreciate, there are a variety of standard methods for creating such a structure-activity relationship. Thus, in some instances, the work may be largely empirical, and in others, the three-dimensional structure of an endogenous polypeptide or portion thereof can be used as a starting point for the rational design of a small molecule compound or compounds.

In some embodiments, test compounds identified as "hits" (e.g., test compounds that demonstrate egr1 binding and/or inhibitory activity) in a first screen are selected and optimized by being systematically altered, e.g., using rational design, to optimize binding affinity, avidity, specificity, or other parameter. Such potentially optimized structures can also be screened using a method described herein. Thus, in one embodiment, the invention includes screening a first library of test compounds using a method described herein, identifying one or more hits in that library, subjecting those hits to systematic structural alteration to create one or more second generation compounds structurally related to the hit, and screening the second generation compound. Additional rounds of optimization can be used to identify a test compound with a desirable therapeutic profile.

Test compounds identified as hits can be considered candidate therapeutic compounds, useful in treating disorders described herein. Thus, the invention also includes compounds identified as "hits" by a method described herein, and methods for their administration and use in the treatment, prevention, or delay of development or progression of a disease described herein.

The invention is further described in the following examples, which do not limit the scope of the invention described in the claims.

EXAMPLES

Example 1

Cy/GCSF Mobilization is Associated with HSC Expansion and Decreased Engraftment Capacity Treatment of mice with cyclophosphamide (Cy) and sequential daily doses of granulocyte-colony stimulating factor (GCSF) induces a 10-12-fold expansion of the hematopoietic stem call (HSC) population in the bone marrow (BM) that peaks by day +2 of the mobilization regimen and proceeds with the subsequent migration (first detectable at day +3 (D+3) of Cy/G treatment) of recently divided HSC from the BM into the peripheral blood (PB) and spleen (Sp) of mobilized animals (Morrison et al., Development. 1997; 124: 1929-1939). This massive expansion is associated with increased self-renewal and an accelerated rate of HSC division, as measured by incorporation into newly synthesized DNA of the thymidine analog bromodeoxyuridine (BrdU). While, as previously reported (Dwight et al., 2001, supra; Cheshier et al., Proc Natl Acad Sci USA. 1999; 96:3120-3125), BM HSC of unmanipulated animals are largely quiescent (<10% of cells in S-G2/M phases of the cell cycle, and only 6% or 24% of HSC becoming BrdU+ at 1 or 12 hours after BrdU injection, respectively), up to 35% of day +2 BM HSC show >2n DNA content, and ~32% or 85% of these cells, respectively, became BrdU+ 1 or 12 hours after injection (FIG. 1A-F). Interestingly, the HSC proliferative burst in the BM in response to Cy/GCSF treatment is not long-lived, and by day +4 of the Cy/GCSF treatment the cell cycle status of BM HSC returns to normal (8.5±1.2% in S-G2/M phase and 7% or 20% of cells incorporating BrdU in 1 or 12 hours, respectively). Migrating HSC, found in the spleen of day +4 mobilized mice continue to proliferate, however, with 20.5±2.3% cells in S-G2/M phase and 17% or 40% BrdU+ cells after 1 or 12 hours, respectively (FIGS. 1A-F). In contrast, as previously demonstrated (Wright et al., Science. 2001; 294:1933-1936), day +4 MPB HSC are largely in G1 phase of the cell cycle and show levels of BrdU incorporation intermediate between day +4 BM and Sp HSC.

Example 2

Position in Cell Cycle Determines HSC Reconstitution Ability

The rapid proliferation of mobilized HSC may have an important impact on their function in hematopoietic reconstitution experiments. Cycling or recently divided HSC, including day +4 MPB or Sp HSC, exhibit substantially reduced capacity for engraftment of lethally irradiated recipients (Morrison et al., 1997, supra; Fleming et al., J Cell Biol. 1993; 122:897-902; Glimm et al., Blood. 2000; 96:4185-4193).

To further study this phenomenon, competitive reconstitution assays were used to examine the engraftment capability of highly purified c-kit$^+$Lin$^-$Sca-1$^+$ Flk2$^-$ (KLSF) and c-kit$^+$Thy1.1$^{lo}$Lineage marker$^-$Sca-1$^+$ (KTLS) HSC, which were double stained with the nucleic acid stains Hoechst 33342 and Pyronin Y, and sorted into G0, G1 or S-G2/M sub-populations. Lethally irradiated Ly5.2+ mice were transplanted with 10 or 50 G0, G1, or S-G2M Ly5.1+ KTLS or KLSF HSC, sorted by the gating parameters shown in FIG. 2A, together with 2×10$^5$ Ly5.2+ BM cells. The percent of Ly5.1+ leukocytes in the PB of recipients was determined by flow cytometry post-transplant at 3-4 week, 9-12 weeks, and after more than 18 weeks. The frequency of recipients showing long-term multilineage reconstitution (LT-MLR) for each population is shown in FIG. 2B.

Sustained, multi-lineage reconstitution was observed primarily in animals transplanted with G0 long-term hematopoietic stem cells (LTHSC) or KTLS HSC (11 of 24 recipients of 10 G0 HSC and 8 of 9 recipients of 50 G0 HSC). Furthermore, transplanted G0 HSC generally showed increasing contributions to hematopoiesis (indicated by increasing PB chimerism) over time, while animals transplanted with either 10 or 50 KLSF or KTLS HSC in either G1 or S-G2/M phases showed little or no contribution to mature PB lineages and none exhibited multilineage reconstitution longer than 12 weeks post-transplant (FIGS. 2A-B).

These data suggest that the ability of HSC to functionally engraft irradiated recipients dramatically decreases as soon as they exit G0. Although the underlying explanation for this loss of engraftment potential remains unclear, it may relate to altered or inefficient BM homing of cycling HSC, as G0, G1, and S-G2/M phase HSC show equivalent proliferative capacity in vitro (data not shown). Such an explanation is further supported by observations in human CD34+ BM progenitor cells, which in G0/G1 phase show increased adhesiveness to stromal cells and appear to migrate to the BM of conditioned recipients with increased frequency over S-G2/M cells, and by our data suggesting an impaired BM homing capacity of recently divided G1-phase MPB HSC. These findings raise the possibility that HSC cell cycle status directly impacts the migration and/or function of HSC, and may have significant implications for the use of cycling cells in PBPC transplantation.

Example 3

Genes Regulating Cell Cycle are Differentially Expressed in Mobilized Hsc and May Signify the Recruitment of Distinct Cell Cycle Machinery in Self-Renewing vs. Differentiating Divisions To begin to address the molecular mechanisms underlying functional differences in mobilized HSC, DNA microarray technology was used to identify changes in gene expression associated with HSC mobilization. Using amplified RNA isolated from 50-100,000 KTLS HSC, double-sorted by FACS from the BM of untreated or day +2 Cy/G-treated mice (C57BL/6-Ka/Thy1.1), the transcription profiles of normal BM HSC and rapidly proliferating day +2 BM HSC were compared. Samples were hybridized to custom 26K or 42K cDNA arrays generated in collaboration among the laboratories of Drs. Irving Weissman, Patrick Brown, David Botstein and Greg Barsh (Stanford University), and the RIKEN Genome Center in Japan, and available through the Stanford Microarray Core Facility (Stanford University). Because day +2 BM HSC represent an HSC population that is undergoing an increased frequency of self-renewing divisions, to expand the HSC population, and is preparing to migrate, to seed the appearance of HSC in the blood and spleen at day +3 of the Cy/GCSF protocol (Morrison et al., 1997, supra), these experiments identity genes and pathways important both in HSC self-renewal and in HSC migration.

Functional classification of the 100 genes most up- or down-regulated in day +2 BM HSC revealed that about half of these encode unknown genes or uncharacterized EST sequences (data not shown). Intriguingly, of the remaining genes with altered expression, many (~30%) encoded transcription factors, signaling proteins, or other genes with known or suspected roles in cell cycle regulation. Using quantitative (real-time) RT-PCR (qRT-PCR, SYBR green detection strategy), we validated the differential expression of several of these genes, and extended this analysis to assay the relative expression levels of additional proliferation-associated genes in untreated, day +2 BM, day +4 BM and day +4 Sp HSC (FIGS. 3A-F and FIGS. 5A-B).

These data reveal the differential expression of a distinct subset of cell cycle regulators by self-renewing, pre-migratory HSC (day +2 BM) as compared with non-cycling, less migratory normal HSC or recently migrated HSC undergoing differentiative divisions (day +4 Sp). In particular, proliferation of day +2 BM HSC appears to be associated with specific induction of the G1-cyclins D3 and E1 (FIGS. 3C-D), while both day +4 BM and Sp HSC show equivalent or reduced expression of G1-phase cyclins, as compared to normal HSC (FIGS. 3A-E). In addition, substantially reduced expression of the immediate early transcription factor, early growth response-1 (egr1) was found (FIG. 3F and FIG. 5A-B). egr1 has been shown to exert cell-type specific effects on cellular proliferation and survival (Thiel and Cibelli, J. Cell. Physiol. 2002; 193:287-292). The microarray and rt-PCR data also revealed that expression of other early immediate-early response genes was also reduced in Day+2 Cy/GCSF treated KTLS HSC, e.g., junB, c-fos, and c-jun, see FIGS. 4 and 5A-B.

Figure 5A:
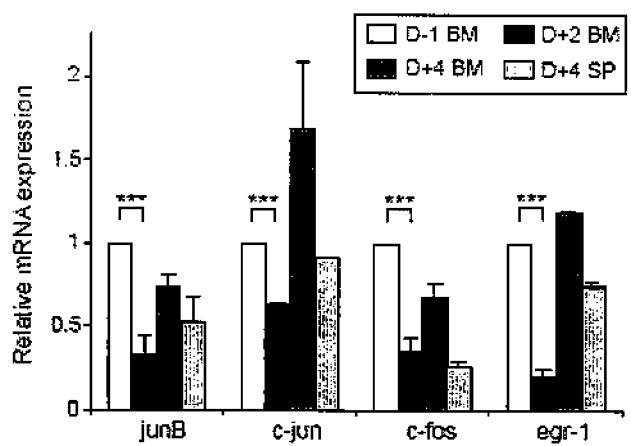
FIG. 5A is a bar graph illustrating the results of real-time PCR analysis of junB, c-jun, c-fos, and egr1 in unmobilized and mobilized KTLS HSC from normal BM, day +2 BM, or day +4 BM, or day +4 Sp.
Figure 5B:
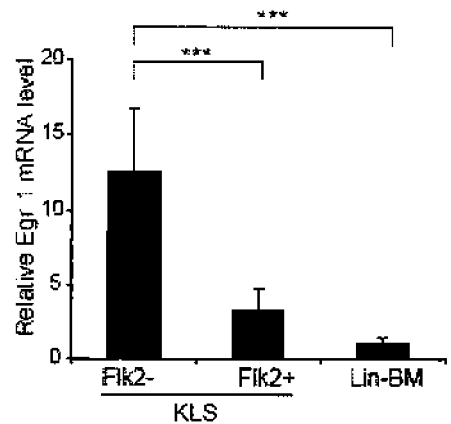
FIG. 5B is a bar graph illustrating levels of Egr1 relative to β-actin mRNA determined by qPCR for lineage-depleted bone marrow (Lin-BM), or for the indicated populations of double-sorted BM cells. Expression of Egr1 is highest among multipotent long-term hematopoietic precursor cells, KLSF HSC (***P≦0.001 by unpaired t-test).

Notably, in unmanipulated mice, Egr1 expression was dramatically elevated specifically among multipotent subsets of mouse BM cells (i.e., those contained within the c-kit$^+$Lin$^-$Sca-1$^+$ (KLS) fraction and capable of contributing to both lymphoid and myeloid cell development). Egr1 expression was highest among the most primitive, most quiescent, long-term- (LT-) reconstituting HSC, defined by the cell surface phenotype KLSFlk2$^-$ (KLSF) (FIG. 5B). Egr1 expression diminished as HSC differentiated to KLSFlk2$^+$ multipotent progenitors (NP), a process that is accompanied by loss of self-renewal potential and an increased rate of proliferation (Adolfsson et al., 2001; Immunity. 15:659-669; Christensen and Weissman, 2001; Proc Natl Acad Sci USA. 98:14541-14546; Forsberg et al., 2006; Cell. 126:415-426; Ito et al., 2000; Exp Hematol. 28:1269-1273; Lai and Kondo, 2006; J Exp Med. 203:1867-1873; Rossi et al., 2005; Proc Natl Acad Sci USA. 102:9194-9199; Yang et al., 2005; Blood. 105: 2717-2723) (FIG. 5B). This selective high-level expression of Egr1 by normal, quiescent HSC, together with its substantial repression during Cy/G-induced HSC expansion and initiation of migration, suggested the intriguing possibility that EGR1 may normally act to control HSC homeostasis in the BM by limiting HSC cell cycle entry and/or by restricting HSC migration.

Example 4

Egr1 Expression in Purified LTHSC, STHSC, and MPP

To farther explore the role of egr1 in HSC mobilization and self-renewal, egr1 expression levels were evaluated in short-term hematopoietic stem cells (STHSC), LTHSC, and MPP. The cells were sorted by immunophenotype using FACS (CD34$^-$Flk2$^-$KLS=LTHSC, CD34$^+$Flk2$^-$KLS=STHSC, and CD34+Flk2+KLS=ST/MPP), and expression levels were quantified using qrt-PCR as described above. Levels were normalized to beta-actin.

Figure 6:
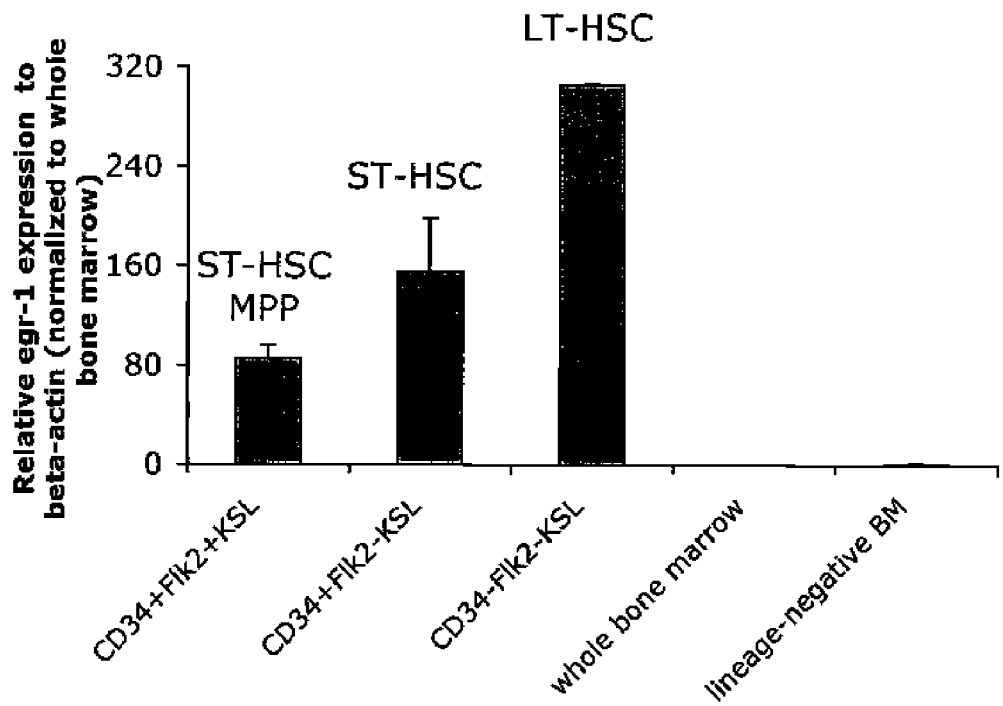
FIG. 6 is a bar graph illustrating the results of RT-PCR showing differential expression of egr1 in different compartments of hematopoietic stem and progenitor cells. Data are given as mean fold differences in expression, normalized for expression of β-actin.

The results are shown in FIG. 6. Expression of egr1 was substantially (p<0.05 by Student's t-test) higher in LTHSC as compared to STHSC; lowest expression levels were seen in MPP.

These results show that egr1 is strongly expressed by multipotent HSC and is repressed during HSC expansion. Thus, egr1 may normally act to restrict HSC entry to the cell cycle and/or to limit HSC migration.

To further evaluate the potential role of these immediate early response transcription factors in regulating HSC proliferation and migration, the relative expression of four members of this gene family (JunB, c-jun, c-fos, and egr1) was determined in KTLS HSC (Morrison and Weissman, 1994; Immunity. 1:661-673; Spangrude et al., 1988; Science. 241:58-62) purified by fluorescence activated cell sorting (FACS) from wild-type mice or from mice treated with a combination of cyclophosphamide (Cy) and granulocyte-colony stimulating factor (G-CSF). Treatment of mice with Cy and sequential daily doses of G-CSF (G) induces rapid and reproducible HSC mobilization, which begins with a massive (10-12-fold) proliferative expansion of HSC in the BM that peaks at day +2 (D+2) of the treatment regimen and proceeds with the subsequent migration (first detectable at day +3 (D+3) of Cy/G treatment) of recently divided HSC from the BM into the peripheral blood (PB) and spleen (SP) of mobilized animals Morrison et al., 1997; Proc Natl Acad Sci USA. 94:1908-1913; Wright et al., 2001; Blood. 97:2278-2285). Significantly, after D2, HSC frequency in the BM declines, and the rate of BM HSC proliferation returns to normal by day +4 (D+4) (Morrison et al., 1997; Proc Natl Acad Sci USA. 94:1908-1913; Passegue et al., 2005; J Exp Med. 202:1599-1611). These data indicate that D+2 Cy/G-treated HSC represent a rapidly expanding, pre-migratory HSC population. Thus, genes differentially expressed by these cells, as compared to untreated, quiescent HSC, are likely to be involved in HSC self-renewal and/or release from the BM environment.

Example 5

Loss of egr1 Increases Frequency and Number of LTHSC

Figure 7A:
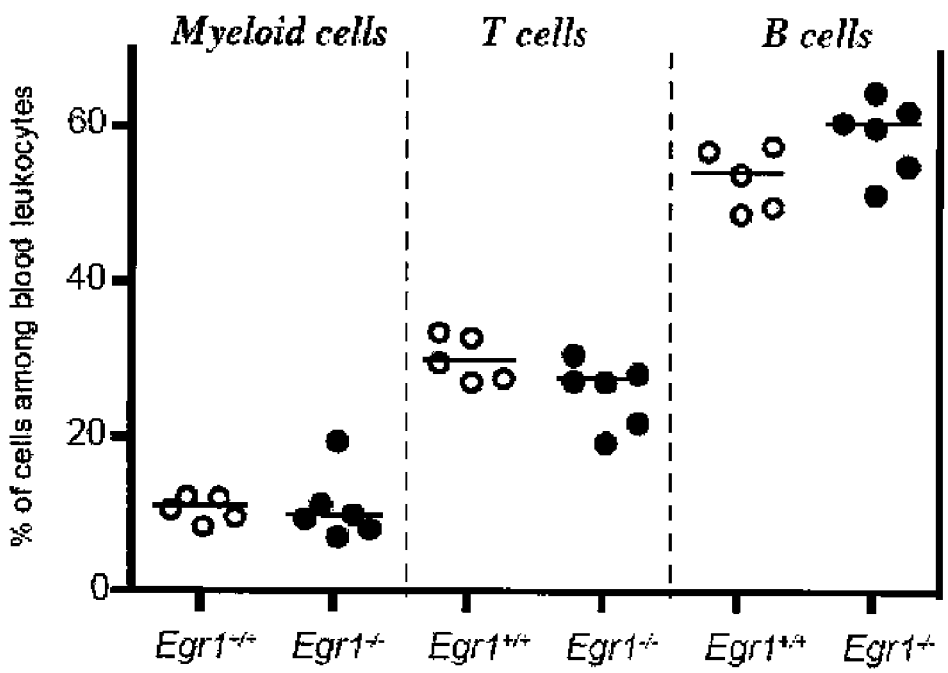
FIG. 7A is a graph illustrating frequencies of circulating mature blood cells in Egr1$^{-/-}$ and wild-type mice. Frequencies of Mac1$^+$Gr1$^+$ granulocytes, CD3/4/8$^+$ T cells, and B220$^+$ B cells were determined by flow cytometric analysis of whole peripheral blood (PB). The median in each analysis is indicated by a horizontal bar (p>0.05).
Figure 7B:
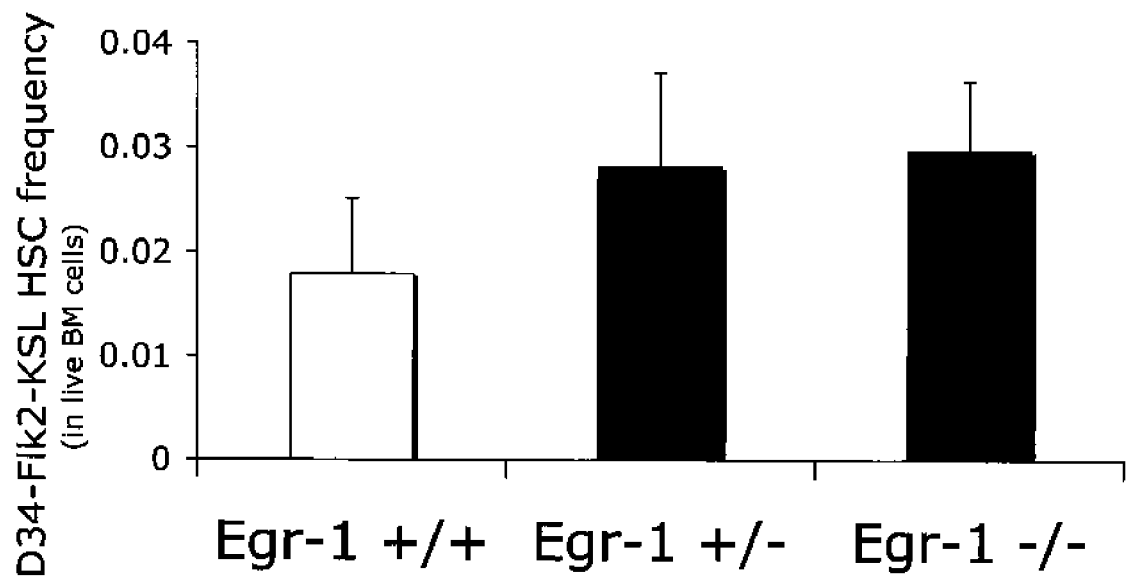
FIG. 7B is a bar graph illustrating frequencies of LTHSCs in the BM of wild type, egr1 KO, and egr1 heterozygous mice. egr1 KO and heterozygous mice appear to have increased frequencies of LTHSCs in the BM.
Figure 8:
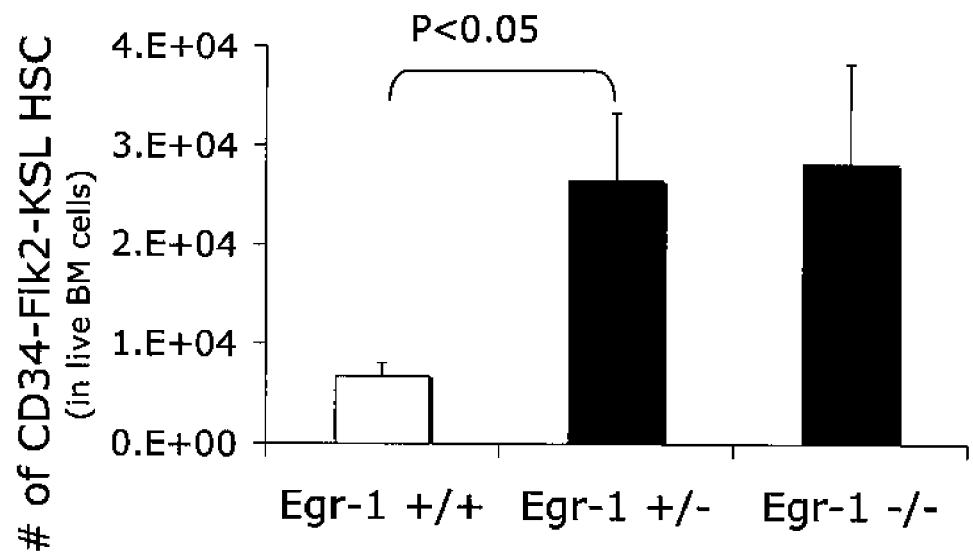
FIG. 8 is a bar graph illustrating total numbers of LTHSCs in the BM of wild type, egr1 KO, and egr1 heterozygous mice. egr1 KO and heterozygous mice appear to have increased numbers of LTHSCs in the BM.

LTHSC are the most desirable cell type for transplantation purposes because they are capable of lifelong production of each and every type of blood cell in the body. To directly evaluate the role of EGR1 in LTHSC maintenance and function, we analyzed Egr1 knockout (Egr1$^{-/-}$) mice (Egr1$^{tm1Jmi}$/Egr1$^{tm1Jmi}$) lacking this transcription factor (Lee et al., 1996; Science. 273:1219-1221; Lee et al.; 1995; J Biol Chem. 270:9971-9977). Previous studies involving Egr1$^{-/-}$ mice have indicated a complete absence of EGR1 protein in these animals, but suggested no gross abnormalities resulting from EGR1 deficiency, aside from female-specific infertility resulting from impaired pituitary production of Luteinizing Hormone β (Lee et al., 1996; Science. 273:1219-1221, Lee et al., 1995; J Biol Chem. 270:9971-9977; Lee et al., 1996b; Mol Cell Biol. 16:4566-4572; O'Donovan et al., 1999; Trends Neurosci. 22:167-173), and modest effects on thymic progenitor cells(Bettini et al., 2002; J Immunol 169:1713-1720; Schnell and Kersh, 2005; Schnell et al., 2006; J. Immunol. 175:2270-2277). There were no alterations in the steady-state levels of mature lymphoid or myeloid cell subsets in the peripheral blood (PB) of Egr1$^{-/-}$ mice (FIG. 7A).

Mice that were either homozygous (egr1$^{-/-}$) or heterozygous (egr1$^{+/-}$) for a null egr1 allele were purchased from Taconic (Germantown, N.Y.; described in Lee et al., J. Biol. Chem. 1997; 270(17):9971-9977). FACS was used to purify CD34$^-$Flk2$^-$KSL LTHSC from the BM and PB, as described above, and to quantify the frequency and number of such cells. Cell frequency was determined by flow cytometric analysis, and used with counts of total bone narrow cells to calculate the total HSC numbers in the BM of mice of each genotype.

The results, shown in FIGS. 7, 8, 10, and 11A-D, demonstrate an increased number of LTHSC in the BM (p<0.05, FIG. 8) (FIGS. 11A-D), and increased frequency of LTHSC in the bone marrow (FIG. 7) and PB (p<0.05, FIG. 10) of egr1$^{-/-}$ and egr1$^{+/-}$ mice.

To determine whether the increases in HSC number in Egr1 deficient mice are due to increased proliferation of LTHSC in the mice, cell cycle determination was performed on the purified LTHSC.

Figure 9A:
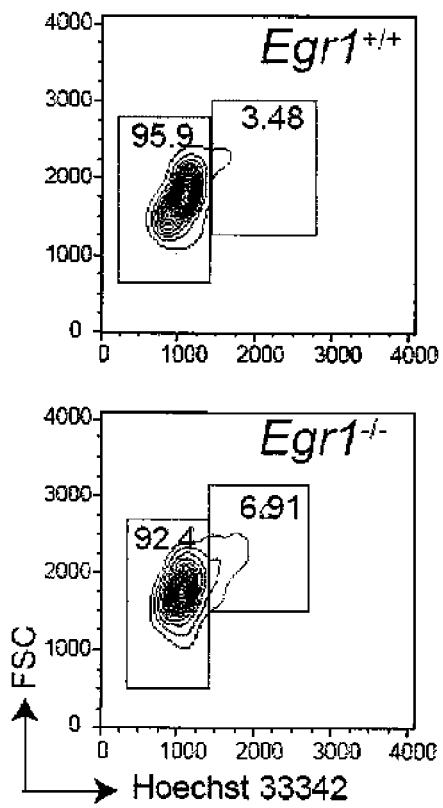
FIGS. 9A-B are representative FACS plots of cell cycle profiles of KLS34- (9A) and KLSF (9B) LT-HSC in Egr1$^{+/+}$ (top) or Egr1$^{-/-}$ (bottom) BM.
Figure 9B:
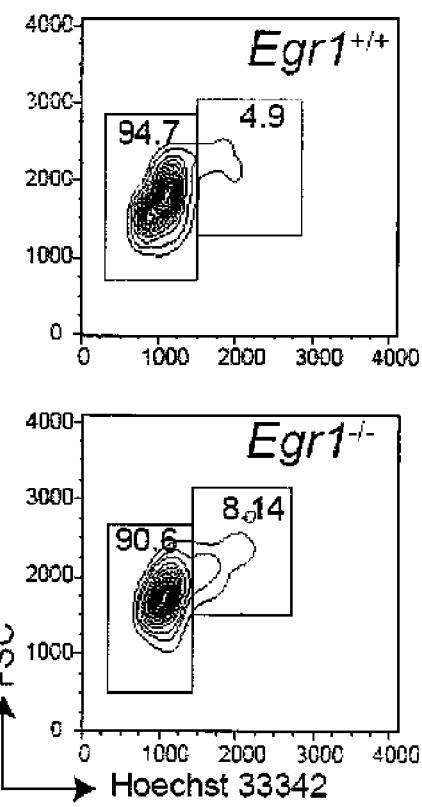
Figure 9C:
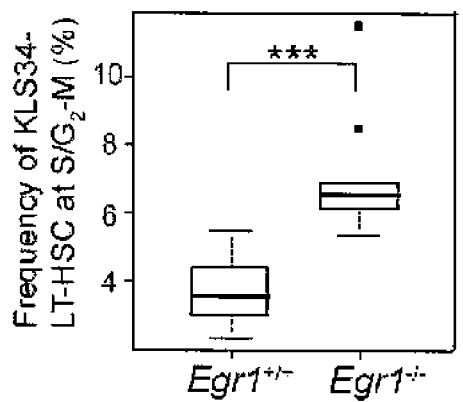
FIGS. 9C-D are box graphs illustrating quantitation of the percentage of KLS34$^-$ (9C) and KLSF (9D) LT-HSC in S/G$_2$-M phases (i.e., >2n DNA content) in Egr1$^{+/+}$ or Egr1$^{-/-}$ (n=7-9) mice (***P≦0.001, by Wilcoxon rank sum test).
Figure 9D:
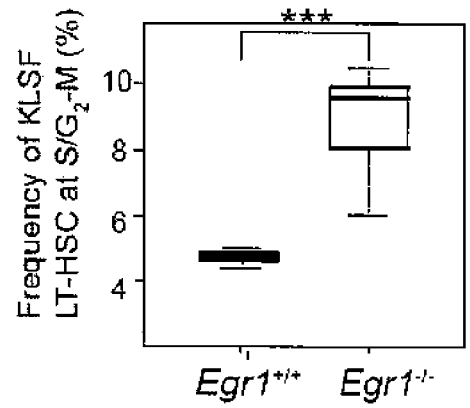
Figure 9E:
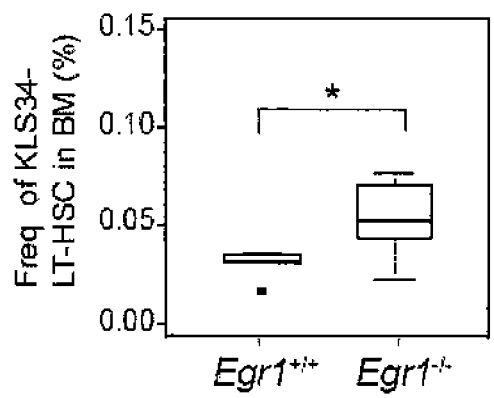
FIGS. 9E-F are box graphs illustrating frequencies of the KLS34- (E) and KLSF (F) LT-HSC in Egr1$^{+/+}$ or Egr1$^{-/-}$ BM were determined by flow cytometry (*P≦0.05 by Wilcoxon rank sum test). (The middle line in each box plot indicates the median value, the upper and lower edges of the box plot are the 75$^{th}$ and 25$^{th}$ percentiles, and the small horizontal bars denote the 75$^{th}$ percentile+1.5*interquartile range and 25$^{th}$ percentile−1.5*interquartile range. Filled circles mark the outliers)
Figure 9F:
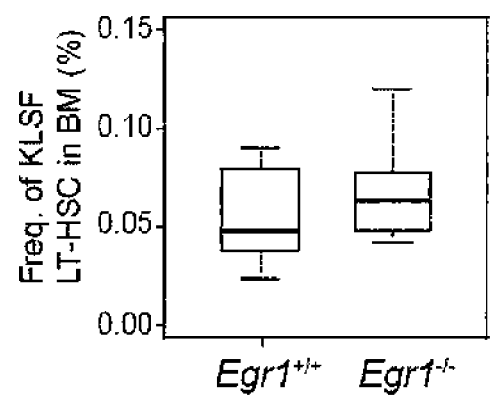
Figure 10:
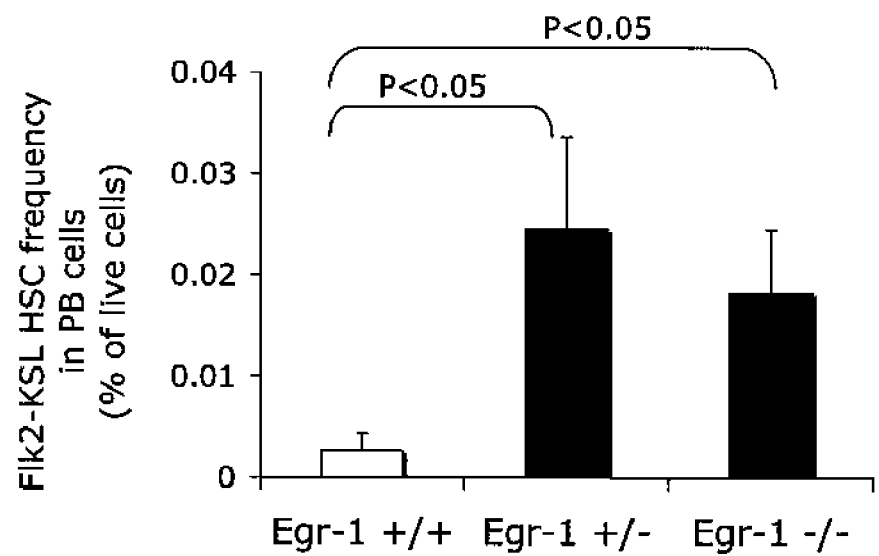
FIG. 10 is a bar graph illustrating the frequency of FLk2-KSL HSC cells in PB cells, expressed as a percentage of live cells. Data represents mean±SEM (n=5, n=6, and n=7 for Egr1+/+, Egr1+/−, and egr1-/− mice, respectively)
Figure 11A:
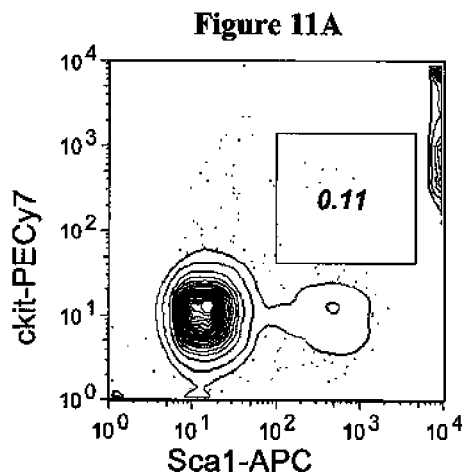
FIGS. 11A-D are FACS plots illustrating the numbers of LTHSC in the PB of wildtype (11A-B) and egr1 KO (11C-D) mice.
Figure 11B:
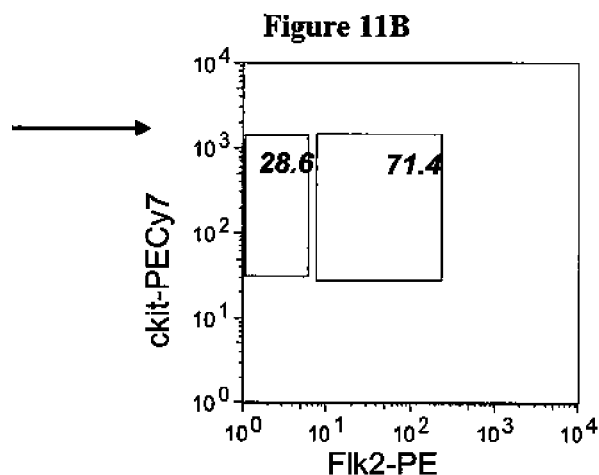
Figure 11C:
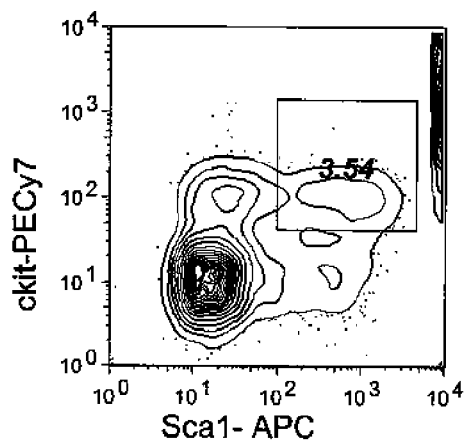
Figure 11D:
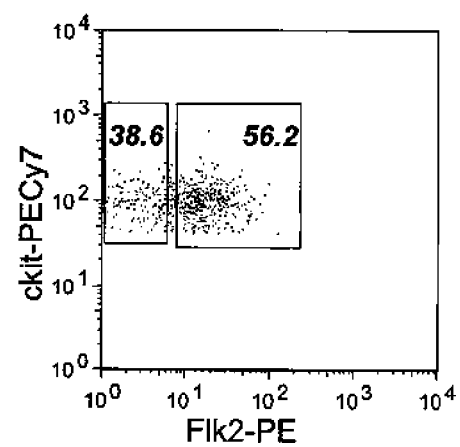
Figure 12A:
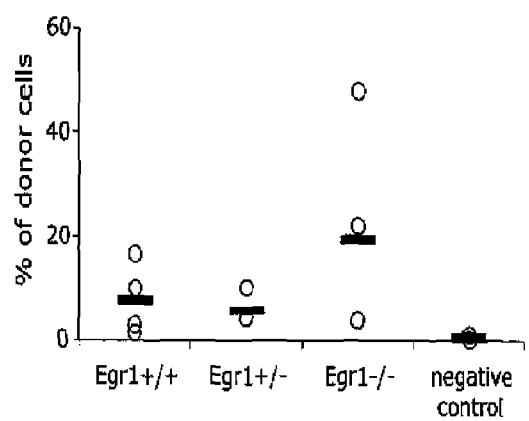
FIGS. 12A-B are dot plots showing the percent of total donor cells (12A) and of donor myeloid cells (12B) in peripheral blood sixteen weeks after of transplantation with whole bone marrow cells from wild-type, egr1 heterozygous, egr1 KO mice, and negative controls.
Figure 12B:
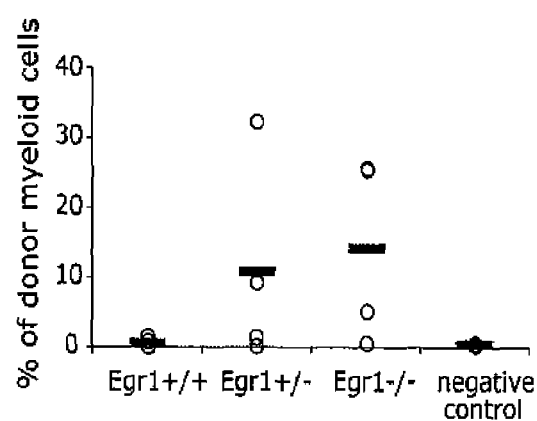

HSC were identified for these studies by cell surface marker profile as either KLS CD34$^-$ (KLS34$^-$) (FIG. 9A, C, F) or KLS Flk2$^-$ (KLSF) (FIG. 9B, D, F) (Adolfsson et al., 2001; supra; Christensen and Weissman, 2001; supra; Ito et al., 2000; supra; Rossi et al., 2005; supra; Yang et al., 2005; supra). Sorted cells were further stained with Hoechst 33342, which labels DNA, and allows discrimination of HSC in distinct stages of the cell cycle: G0 and G1 stage cells exhibit 2n DNA content (determined by Hoechst staining), while S/G2/M phase cells have >2n DNA content. Hoechst 33342 (Ho) staining for DNA content (Passegue et al., 2005; Cell. 119:431-443) of sorted HSC revealed an approximately two-fold increase in the percent of Egr1$^{-/-}$ HSC in S-G$_2$/M phases of the cell cycle, when compared with wild-type controls (FIG. 9C, D) (***P≦0.001 by Wilcoxon rank sum test; n=7-9). Despite this consistent increase in steady-state HSC proliferation, Egr1$^{-/-}$ mice showed only subtle changes in the overall frequency and number of HSC in the BM. Flow cytometric analysis determined that the average frequency of LTHSC, defined by the marker profile KLS34$^-$ (Adolfsson et al., 2001; supra; Christensen and Weissman, 2001; supra; Ito et al., 2000; supra; Rossi et al., 2005; supra; Yang et al., 2005; supra), was increased by ~80% (1.8 fold) in Egr1$^{-/-}$ mice as compared to wild-type (Egr$^{+/+}$) littermates (FIG. 9E, *P=0.02 by Wilcoxon rank sum test, n=5-8). However) consistent with previous reports (Schnell et al., 2006; J. Immunol. 175:2270-2277), steady-state frequencies of the KLSF population was not significantly altered in Egr1$^{-/-}$ BM (FIG. 9F, P=0.27 by Wilcoxon rank sum test, n=9-12).

Thus, enhanced proliferative activity among Egr1$^{-/-}$ HSC does not lead to substantial accumulation of these cells, suggesting the existence of additional regulatory mechanisms to control HSC expansion in these mice.

Example 6

Inhibition of egr1 Increases Functional LTHSC

To determine whether the increase in LTHSC in the PB and BM resulting from the loss of egr1 translated into an increase in functional LTHSC, which are useful in HSC transplantation, an animal model of cell transplantation was used.

Figure 13A:
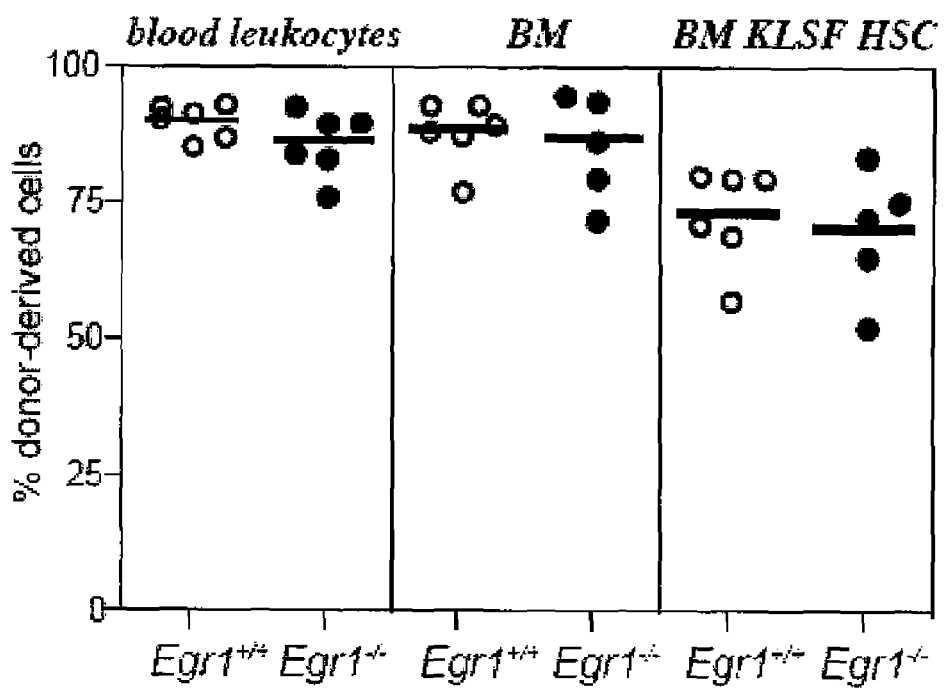
FIG. 13A is a dot plot showing the percent of donor-derived myeloid cells in recipients of peripheral blood cells from transplantation with donor peripheral blood cells of egr1 wild type (open circles) or egr1 KO (filled circles) mice (noncompetitive BM transplantation). Lethally irradiated congenic CD45.1+ or F1 recipients received 500,000 CD45.2+ WBM cells from Egr1+/+ or Egr1-/- mice without helper BM cells. The percent of donor-derived hematopoietic cells in the blood, BM, and KLSF LT-HSC in the BM of individual recipient at 8 weeks post-transplant is plotted as a circle, with the median value shown as a horizontal bar. Data are combined from two separate experiments.
Figure 13F:
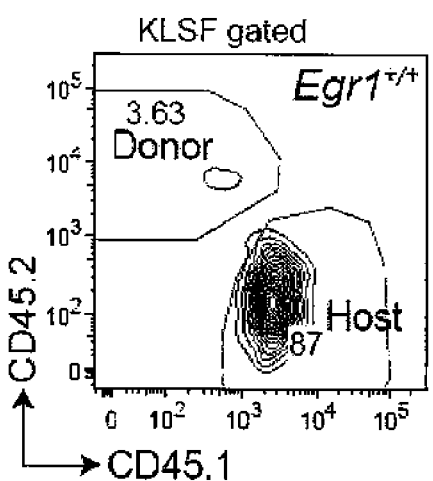
FIGS. 13F-I are FACS plots showing that wild-type recipients of Egr1$^{-/-}$ BM cells have increased long-term engraftment of HSC. Lethally-irradiated CD45.1+ wild-type mice were given transplantation with 25,000 WBM cells from either CD45.2+ Egr1$^{+/+}$ or Egr1$^{-/-}$ mouse, along with 200,000 CD45.1+ competitor WBM cells. 30 weeks after transplantation, WBM cells from the recipient of Egr1$^{+/+}$ (13F and H) or Egr1$^{-/-}$ (13G and I) donor cells were analyzed for donor KLSF LT-HSC (13F-G) and hematopoietic cell (13H-I) chimerism in the BM by flow cytometry.
Figure 13G:
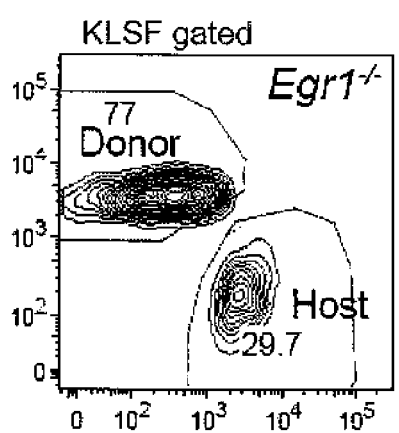
Figure 13H:
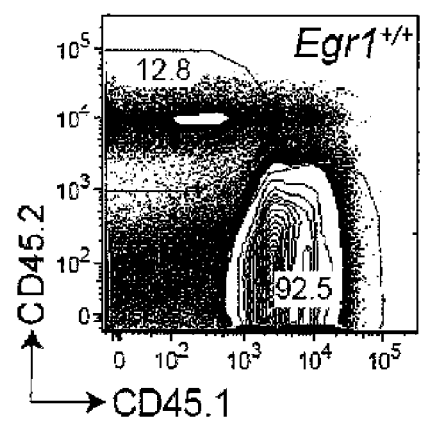
Figure 13I:
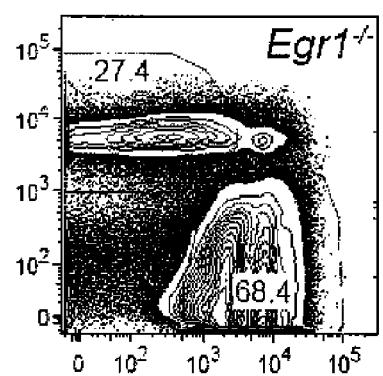

To assay the functional activity of LTHSC in Egr1$^{-/-}$ mice, noncompetitive transplantation assays were employed in which "test" cells could be distinguished from the host cells by expression of distinct congenic markers on hematopoietic cells (CD45.2 and CD45.1) (Domen and Weissman, 1999; Mol Med Today. 5:201-208). 0.5×10$^6$ CD45.2$^+$ whole bone marrow (WBM) cells from Egr1$^{+/+}$ or Egr1$^{-/-}$ mice were transplanted intravenously into lethally irradiated congenic CD45.1$^+$ or F1 recipients. Eight weeks after transplantation, donor Egr1$^{-/-}$ BM cells showed high levels of contributions to mature and immature hematopoietic cells within circulating blood and BM in the recipients comparable to the recipients of donor Egr1$^{+/+}$ BM cells. Recipients of Egr1$^{-/-}$ and Egr1$^{+/+}$ BM also exhibited a similar magnitude of contribution to the primitive subset of BM KLSF LTHSC by donor BM cells (FIG. 13A).

To quantitatively measure and compare the level of long-term multilineage reconstitution by LTHSC in Egr1$^{-/-}$ mice and wild-type controls, we performed competitive BM transplantation with limiting numbers (25,000 or 100,000) of unfractionated BM cells from Egr1$^{+/+}$ or Egr1$^{-/-}$ mice, together with 200,000 competitor Egr1$^{+/+}$ BM cells, into lethally irradiated congenic recipients. As shown in FIGS. 13C-E, BM cells from both Egr1$^{+/+}$ and Egr1$^{-/-}$ donors contributed to the reconstitution of mature PB myeloid, B, and T cells, as assayed by flow cytometry.

When 25,000 WBM cells were transplanted as donors at a 1:8 ratio of donor:competitor cells (which contain, on average, 8-14 and 9-17 LTHSC in Egr1$^{+/+}$ and Egr1$^{-/-}$ WBM cells, respectively, by phenotype (FIGS. 2C-D)), long-term (at least 19 weeks) multi-lineage reconstitution was greater among recipients of Egr1$^{-/-}$ (7 of 10 (70%)) than animals receiving Egr1$^{+/+}$ (2 of 9 (22%)) BM cells (p0.07 by Fisher's exact test). More than half of the recipients of Egr1$^{+/+}$ BM cells did not have long-term myeloid lineage reconstitution by donor cells (6 of 9 (67%)), contrary to recipients of Egr1$^{-/-}$ BM cells (*p$\leq$0.05 by Wilcoxon rank sum test) (FIG. 13C). Because of the short half-life (~24 hrs) of myeloid cells, donor-derived myeloid cell production in long-term is well known to correlate with the activity of donor-derived HSC (Wright et al., Science. 2001; 294(5548):1933-6).

To confirm that the donor myeloid cell chimerism reflects donor BM HSC chimerism in long-term, mice were sacrificed 30 weeks after transplantation and analyzed for BM HSC chimerism in these recipients (FIGS. 13F-I). Our data support that recipients of 25,000 donor Egr1$^{-/-}$ BM cells led to higher long-term HSC engraftment than those of Egr1$^{+/+}$ BM cells. Transplantation with an increased number (100,000) of donor Egr1$^{-/-}$ or Egr1$^{+/+}$ BM cells revealed that the average frequencies of reconstituting donor-derived cells in recipients of Egr1$^{-/-}$ or Egr1$^{+/+}$ BM cells were in the similar range FIG. 13B-E).

These data suggest that Egr1$^{-/-}$ mice, compared to Egr1$^{+/+}$, have modestly increased numbers of functional HSC in the BM in which this difference in numbers can be manifested by BM cell transplantation with limited number of donor BM cells.

Taken together, the data described herein provide evidence that loss of EGR1 activity in Egr1$^{-/-}$ mice does not impair their reconstitution capacity, and may enhance their function in long-term hematopoietic repopulation when donor cell number is limited.

Example 8

Spontaneous, Constitutive Mobilization of HSC in Egr1-/- Mice

As discussed above, the relative lack of expansion of BM LTHSC in Egr1$^{-/-}$ mice despite significant increases in the proliferative fraction of this population implies that additional regulatory mechanisms act to limit HSC accumulation in the BM of these mice. In this regard, we were intrigued by the substantial downregulation of Egr1 expression in pre-migratory BM HSC purified from D+2 Cy/G-treated mice. Because D+2 Cy/G HSC represent an USC population that is just about to migrate from the BM and into the PB (Morrison et al., 1997, Proc Natl Acad Sci USA. 94:1908-1913), these data suggested that EGR1 may also play a role in retaining HSC in the BM. Thus, we hypothesized that HSC frequency in the BM could be maintained at near normal levels in Egr1$^{-/-}$ mice by enhancing the release of "excess" HSC from the BM.

Figure 14A:
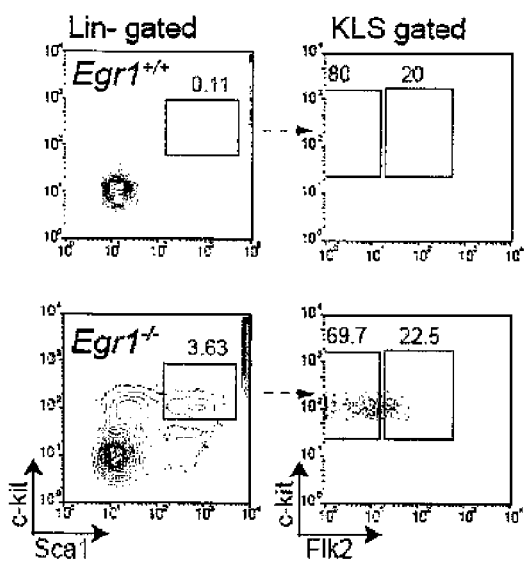
FIG. 14A is a set of four representative FACS plots depicting higher frequencies of KLSF LT-HSC in Egr1$^{+/+}$ (top row) vs. Egr1$^{-/-}$ (bottom row). Plots on the left were first gated on Lin$^-$ PB leukocytes. Plots on the right show events in the c-kit$^+$Sca-1$^+$ gate (shown on the left). Numbers above each gate show the percentage of events within the gate.
Figure 14B:
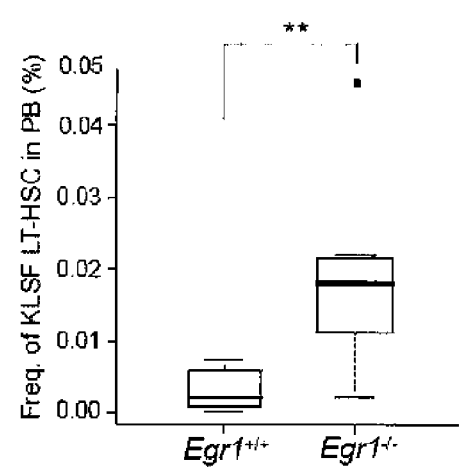
FIG. 14B is a box plot of quantitation of the overall frequency (% of live PB leukocytes) of KLSF LT-HSC in the PB of Egr1$^{+/+}$ or Egr1$^{-/-}$ mice. HSC frequencies were determined by flow cytometry, with median (horizontal bar) shown on the box plot. Differences between Egr1$^{-/-}$ and Egr1$^{+/+}$ mice are significant (**P≦0.01 by Wilcoxon rank sum test).
Figure 14C:
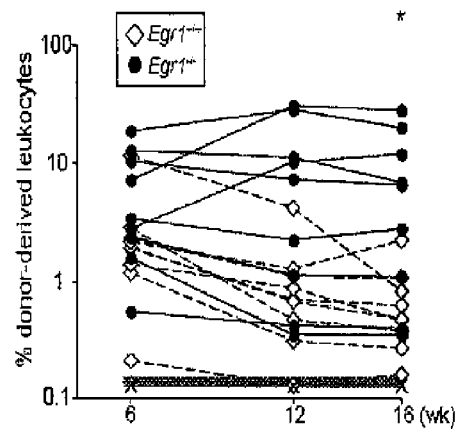
FIGS. 14C-F are line graphs illustrating enhanced engraftment of recipient mice by Egr1$^{-/-}$ PB cells. Lethally irradiated congenic recipients received 3×10$^6$ whole PB cells from Egr1$^{+/+}$ (◇, dashed lines) or Egr1$^{-/-}$ (●, solid lines) recipients, together with 3×10$^5$ "host"-type BM cells. Data are plotted as the % donor-derived total blood leukocytes (14C), Mac1$^+$Gr1$^+$ myeloid cells (14D), CD3/4/8$^+$ T cells (14E), or B220$^+$ B cells (14F), as determined by flow cytometry analysis of recipient PB at 6, 12, 16 weeks post-transplant. Transplantion with Egr1$^{-/-}$ and Egr1$^{+/+}$ PB cells displayed significant difference in the recipients (**p≦0.01. *p≦0.05 at week 16). Data are combined from two independent transplant experiments for total of 9 animals per genotype. (Gray line indicates the background level of staining in each analysis, determined by the average+1.5*standard deviation of the negative controls at week 16).
Figure 14D:
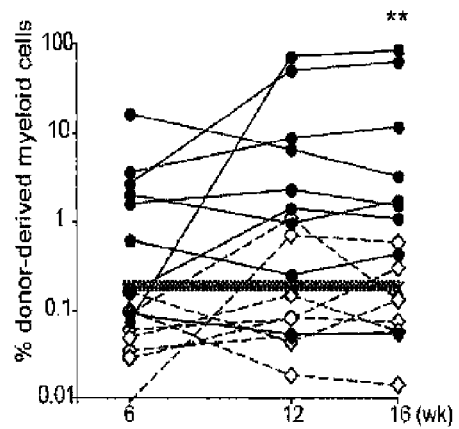
Figure 14E:
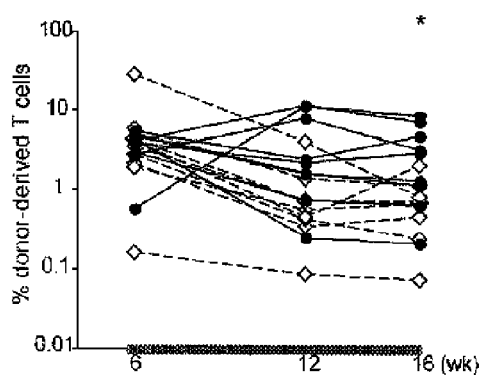
Figure 14F:
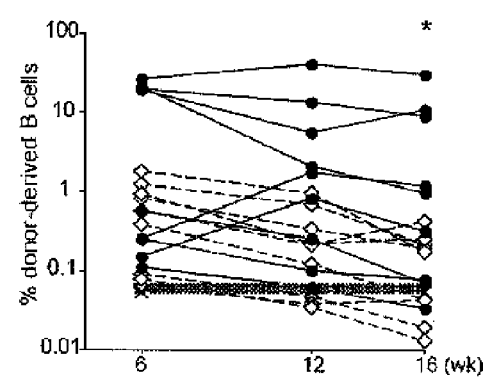
Figure 14G:
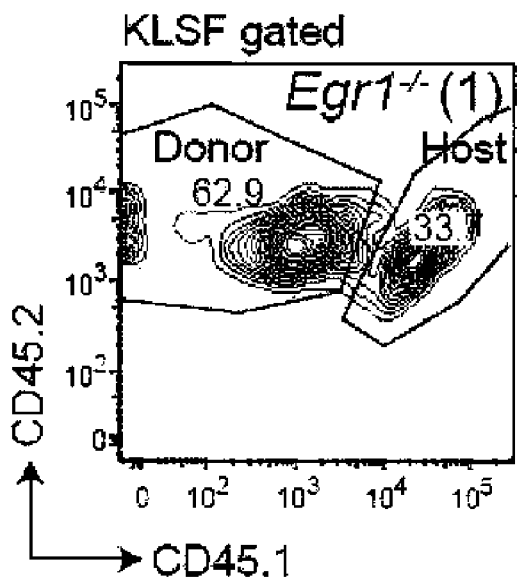
FIGS. 14G-H are representative FACS plots demonstrating that Egr1$^{-/-}$ total blood cells lead to high engraftment of LT-HSC in the BM. 3×10$^6$ CD45.2+PB cells from Egr1$^{-/-}$ donors were transplanted into lethally-irradiated CD45.1+ CD45.2+F1 recipients, together with 3×10$^5$ F1 BM cells. After 20 weeks of transplantation, transplant recipients were sacrificed and the BM cells were analyzed for measurement of the percentage of donor-derived KLSF HSC.
Figure 14H:
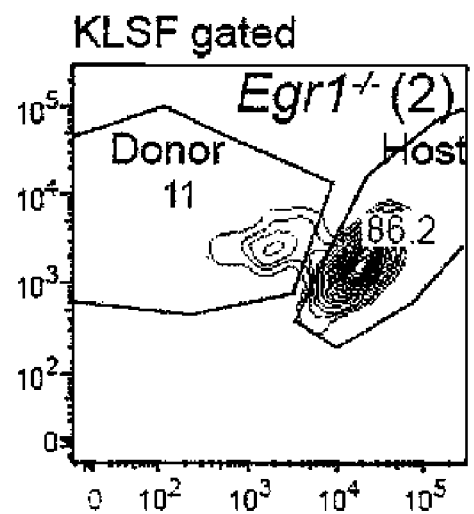

To test the impact of loss of EGR1 function on the localization of LTHSC, we analyzed LTHSC frequency in the bloodstream of wild-type (Egr1$^{+/+}$) and Egr1$^{-/-}$ mice. Consistent with previous findings (Fleming et al., 1993; Proc Natl Acad Sci USA. 90:3760-3764; Morrison et al., 1997; Proc Natl Acad Sci USA. 94:1908-1913; Wright et al., 2001; Science. 294:1933-1936), circulating LTHSC were extremely rare in the PB of wild-type Egr1$^{+/+}$ mice; however, in Egr1$^{-/-}$ mice both the frequency and total number of circulating USC were dramatically increased (up to 10-fold; p=0.01 by Wilcoxon rank sum test), as indicated by flow cytometric analysis of PB for cells exhibiting HSC markers (KLSF or KLSF34$^-$; FIG. 14A-B and data not shown). We further confirmed this striking increase in circulating LTHSC in Egr1 knockout mice by transplantation into lethally irradiated recipients of PB leukocytes from Egr1$^{+/+}$ or Egr1$^{-/-}$ mice. Both Egr1$^{+/+}$ and Egr1$^{-/-}$ PB contributed to myeloid and lymphoid (C and B cell) lineages in a subset of reconstituted mice (FIG. 14C-F). However, 16 weeks after transplant, only 2 of 9 (22%) recipients of Egr1$^{+/+}$ cells maintained multi-lineage hematopoietic chimerism, in contrast to 8 of 9 (89%) Egr1$^{-/-}$ recipients (P=0.02 by Fisher's exact test). At 16 week post-transplant, Egr1$^{-/-}$ PB cells had superior myeloid and lymphoid (T and B) engraftment to Egr1$^{+/+}$ PB cells in recipients (p=0.005, 0.04, and 0.05 for myeloid, T, and B cells, respectively, by Wilcoxon rank sum test). We confirmed that recipients, which displayed high level of myeloid lineage reconstitution by Egr1$^{-/-}$ PB cells had essentially the same level of contribution to KLSF LTHSC in BM (FIG. 14G-H). Overall, these findings show that Egr1$^{-/-}$ mice have markedly increased number of functionally active LTHSC in their circulating blood. Table 1 shows the percent of donor hematopoietic cell chimerism in PB analyzed at 16 weeks of transplantation in these animals.

TABLE 1

|  |  | Egr1$^{-/-}$ (#1) | Egr1$^{-/-}$ (#2) |
| --- | --- | --- | --- |
| % donor cell chimerism | Total leukocytes | 12.2% | 2.81% |
|  | Myeloid cells | 64.4% | 11.8% |
|  | T cells | 2.92% | 1.13% |
|  | B cells | 1.15% | 0.31% |

Figure 14I:
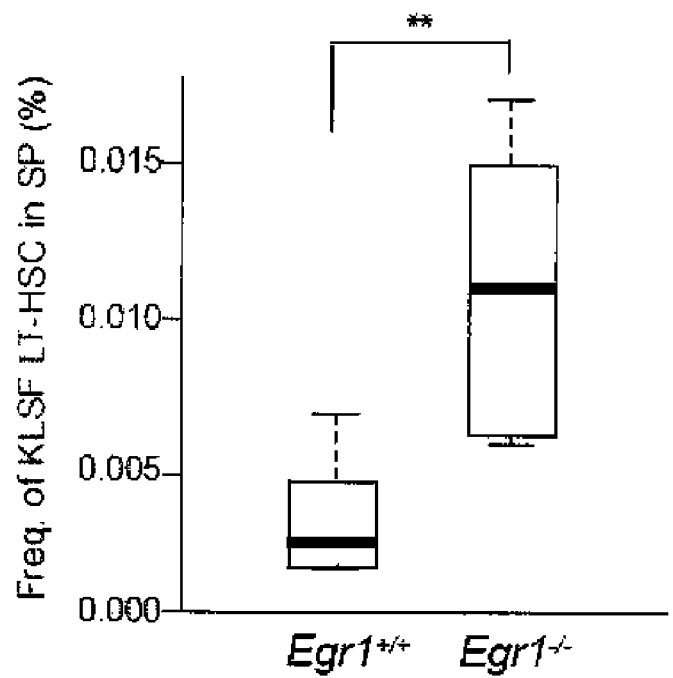
FIG. 14I is a box plot showing that Egr1 deficiency in the hematopoietic system alone leads to spontaneous mobilization of LT-HSC. 5×105 CD45.2+ BM cells from either Egr1-/- or Egr1+/+ donors were transplanted into lethally-irradiated CD45.1+ or CD45.1+CD45.2+F1 recipients. 8 wks. post-transplant, SP of recipient mice were analyzed for the frequencies of KLSF LT-HSC among donor SP cells by flow cytometry. All recipients exhibited ~73-95% contributions of donor-derived cells in their BM (FIG. 4A). Recipients of Egr1-/- donor BM cells showed increased HSC migration to periphery. Data are combined from two independent transplant experiments (n=6 each for recipients of Egr1+/+ or of Egr1-/- BM; **P=0.01).

To test whether increases in circulating HSC in Egr1$^{-/-}$ mice resulted from loss of Egr1 in hematopoietic or in non-hematopoietic cells, we also analyzed chimeric mice transplanted 8 weeks previously with either Egr1$^{+/+}$ or Egr1$^{-/-}$ BM cells (as in FIG. 13A). Similar to Egr1$^{-/-}$ mice, wild-type mice reconstituted with Egr1$^{-/-}$ BM cells showed an increased frequency of HSC among peripheral donor hematopoietic cells (p=0.01 by Wilcoxon rank sum test)(FIG. 14I). These data strongly suggest that hematopoietic loss of EGR1 activity promotes spontaneous mobilization of functional HSC from the BM and into the circulation.

Example 9

Inhibition of egr1 Results in Increased Contribution to T and B Cell Lineages

Figure 15A:
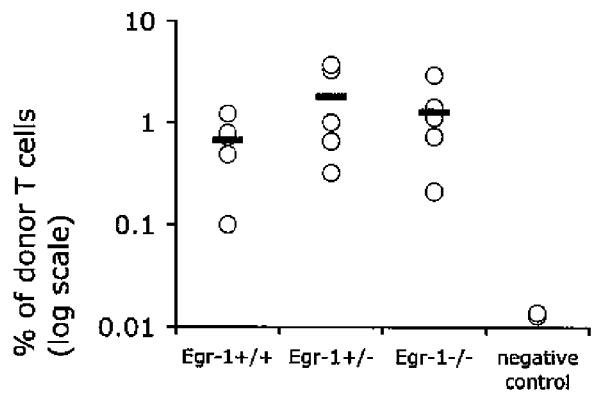
FIGS. 15A-B are dot plots showing the percent of donor T cells (15A) and donor B cells (15B) in wild-type recipients transplanted with peripheral blood cells from donor egr-1 wild type, heterozygous or egr-1 KO. Untransplanted negative control mice are shown for comparison.
Figure 15B:
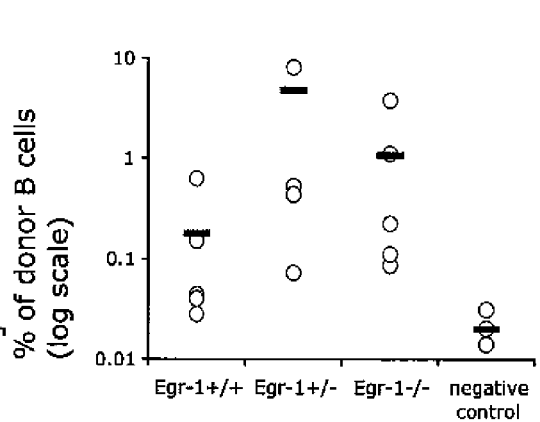

To determine whether the mice that received competitive PB transplants from egr1 wild type and transgenic mice also had increased numbers of T and/or B cells from the transgenic mice, the fraction of T and B donor cells that were of transgenic origin was evaluated using flow cytometric analysis of CD45 allotype and lineage markers, as described above. The results, shown in FIGS. 15A and B, demonstrate that, as for the LTHSC, egr1 transgenic mice also have increased contributions to T and B cell lineages, indicating that the enduring engraftment of multi-lineage reconstituting LTHSC in these mice. The higher contribution of transplanted cells from egr1 knockout or heterozygous donors indicates a higher initial frequency of LTHSC among the donor PB or BM cells and is consistent with the results of direct immunophenotypic analysis of LTHSC frequency and number described above (Example 5, FIGS. 7 and 8).

Example 9

Cy/GCSF-Induced Mobilization in Egr1 KO mice

To evaluate whether the effect of inhibition of egr1 is additive to the mobilization seen in response to stimulation with Cy/GCSF treatment, wild-type and egr1 knockout mice were treated with Cy/GCSF as described above, and the frequency of Flk2-KSL LTHSC in the PB was determined using FACS.

Figure 16:
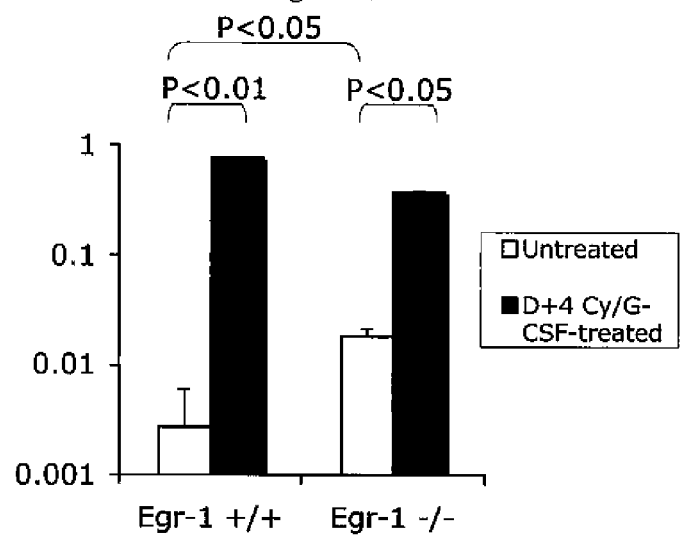
FIG. 16 is a bar graph illustrating the frequency of Flk2-KSL HSC cells in the peripheral blood (PB) of wild type and egr1 KO mice, expressed as a percent of live PB cells, on a log scale, either before (open bars) or after (filled bars) treatment with Cy/G to mobilize HSC.

The results, shown in FIG. 16, indicate that Cy/GCSF-induced mobilization of LTHSC into the PB is not fin-her enhanced in egr1$^{-/-}$ mice. This finding is consistent with the observation that Cy/GCSF treatment itself results in a decrease in egr1 expression (FIGS. 5A-B) and suggests that these two mobilization strategies may exploit similar signaling pathways. Alternatively, because LTHSC in egr1 knockout mice, which are normally present in the bone marrow at a higher overall number than in wild-type mice, do not show equivalently enhanced numbers of mobilized cells in response to Cy/GCSF, these data also may suggest that egr1$^{-/-}$ HSCs exhibit an increased susceptibility to hematopoietic stress or manifest a change in the kinetics of the mobilization response.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of increasing the number of hematopoietic stem cells (HSC) in a subject, comprising administering to a subject in need of increased numbers of HSCs an effective amount of an inhibitory nucleic acid of early growth response-1 (egr1).

2. The method of claim 1, wherein the number of hematopoietic stem cells (HSC) in the bone marrow of the subject is increased.

3. The method of claim 1, wherein the number of hematopoietic stem cells (HSC) in the peripheral blood of the subject is increased.

4. The method of claim 1, wherein the inhibitory nucleic acid is selected from the group consisting of an egr1 specific antisense, an egr1 specific siRNA, an egr1 specific DNAzyme, an egr1 specific ribozyme, and an egr1 specific competitive inhibitor.

5. The method of claim 1, further comprising obtaining bone marrow cells or peripheral blood cells from the subject.

6. The method of claim 5, further comprising administering all or a subset of the bone marrow cells or peripheral blood cells to a subject in need thereof.

7. The method of claim 5, further comprising separating stem cells from the bone marrow or peripheral blood.

8. The method of claim 7, further comprising administering the stem cells to a subject in need thereof.

9. The method of claim 6, wherein the subject in need thereof is the same subject from which the cells were obtained from a HLA type-matched subject.

10. The method of claim 1, further comprising administering to the subject an HSC mobilizing agent selected from the group consisting of interleukin-17 (IL-17), AMD3100, cyclophosphamide (Cy), Docetaxel (DXT), and granulocyte-colony stimulating factor (GCSF).

11. The method of claim 1, wherein the subject in need of increased numbers of HSCs is a subject who has cancer.

12. The method of claim 1, wherein the subject in need of increased numbers of HSCs is a subject who has a hematopoietic neoplastic disorder.

13. The method of claim 1, wherein the subject in need of increased numbers of HSCs is a subject who has an autoimmune disease.

14. The method of claim 1, wherein the subject in need of increased numbers of HSCs is a subject who has a non-malignant disorder.

15. The method of claim 1, further comprising determining the number of HSC in the subject.

16. The method of claim 1, further comprising obtaining HSCs from a first subject; contacting the HSCs with an effective amount of said inhibitory nucleic acid of egr1, to thereby obtain an increased population of HSCs; and administering to the first or a second subject all or a portion of the population of HSCs.

17. The method of claim 16, wherein all or a portion of the population of HSCs is administered to the first subject.

* * * * *